United States Patent [19]

Hubele

[11] Patent Number: 5,102,445
[45] Date of Patent: Apr. 7, 1992

[54] USE OF QUINOLINE DERIVATIVES FOR THE PROTECTION OF CULTIVATED PLANTS

[75] Inventor: Adolf Hubele, Magden, Switzerland

[73] Assignee: Ciba-Geigy Corporation, Ardsley, N.Y.

[21] Appl. No.: 651,119

[22] Filed: Feb. 5, 1991

Related U.S. Application Data

[60] Continuation of Ser. No. 239,861, Sep. 2, 1988, abandoned, which is a division of Ser. No. 868,372, May 27, 1986, Pat. No. 4,902,340, which is a continuation of Ser. No. 663,739, Oct. 22, 1984, abandoned, which is a continuation-in-part of Ser. No. 539,604, Oct. 6, 1983, abandoned, which is a continuation-in-part of Ser. No. 490,912, May 2, 1983, abandoned.

[30] Foreign Application Priority Data

May 7, 1982 [CH] Switzerland .................. 2841/82

[51] Int. Cl.⁵ ................. A01N 43/42; C07D 215/24
[52] U.S. Cl. ........................................ 71/94; 546/178
[58] Field of Search ................... 71/94; 546/178

[56] References Cited

U.S. PATENT DOCUMENTS

| | | | |
|---|---|---|---|
| 4,350,521 | 9/1982 | Böhner et al. | 71/94 |
| 4,602,932 | 7/1986 | Handte et al. | 71/94 |
| 4,749,406 | 6/1988 | Martin | 71/94 |

FOREIGN PATENT DOCUMENTS

| | | |
|---|---|---|
| 0159290 | 10/1985 | European Pat. Off. |
| 0258184 | 3/1988 | European Pat. Off. |
| 2546845 | 4/1977 | Fed. Rep. of Germany |
| 3404401 | 8/1985 | Fed. Rep. of Germany |

OTHER PUBLICATIONS

Boehner et al., *Herbicidal Unsaturated Esters of Halogenated 4-(2-Pyridyloxy)-α-Phenoxypropionic Acids*, EP Application 3,114, 7/25/79 (CA 92:41771v).
Soliman et al., Chemical Abstract, vol. 92, p. 36 (1980).
Jakubke et al., Chemical Abstract, vol. 79, p. 118 (1973).
Levi et al., Chemical Abstract, vol. 79 (1973).
Soliman et al., Journal of Pharmaceutical Sciences, vol. 68, No. 11, pp. 1377-1381.

*Primary Examiner*—Richard L. Raymond
*Assistant Examiner*—S. Mark Clardy
*Attorney, Agent, or Firm*—Edward McC. Roberts

[57] ABSTRACT

In the method of protecting cultivated plants from the harmful effects of agrochemicals, quinoline derivatives of the formula

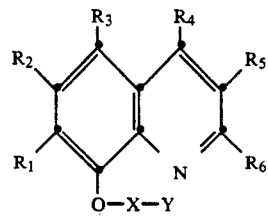

in which $R_1$, $R_2$ and $R_3$ independently of one another are hydrogen, halogen, nitro, cyano, alkyl or alkoxy, $R_4$, $R_5$ and $R_6$ independently of one another are hydrogen, halogen or alkyl, X is an aliphatic, acyclic, saturated hydrocarbon radical having 1 to 3 carbon atoms and Y is a carboxyl group, or a salt thereof, a mercaptocarbonyl group or a salt thereof, a carboxylic acid ester group, a carboxylic acid thiolester group, an unsubstituted or substituted carboxylic acid amide group, a cyclised, unsubstituted or substituted derivative of a carboxylic acid amide group or a carboxylic acid hydrazide group, or X and Y together are an unsubstituted or substituted tetrahydrofuran-2-one ring, including acid addition salts and metal complexes thereof, or compositions containing such derivatives, are used. Novel quinoline derivatives and their preparation are also descirbed.

8 Claims, No Drawings

USE OF QUINOLINE DERIVATIVES FOR THE PROTECTION OF CULTIVATED PLANTS

CROSS-REFERENCE TO RELATED APPLICATION

This application is a continuation of application Ser. No. 239,861, filed Sept. 2, 1988, now abandoned, which is a division of application Ser. No. 868,372, filed May 27, 1986, now U.S. Pat. No. 4,902,340, issued Feb. 20, 1990, which is a continuation of application Ser. No. 663,739, filed Oct. 22, 1984, now abandoned, which is a continuation-in-part of application Ser. No 539,604, filed Oct. 6, 1983, now abandoned, which is a continuation-in-part of application Ser. No. 490,912, filed May 2, 1983, now abandoned.

The present invention relates to the use of quinoline derivatives for protecting cultivated plants from the harmful effect of agrochemicals, compositions containing these quinoline derivatives, novel quinoline derivatives and the preparation of the quinoline derivatives. The quinoline derivatives can also be used for regulating plant growth.

When agrochemicals, such as plant protection agents and especially herbicides, are used, the cultivated plants may be damaged to a certain degree, depending on factors such as, for example, the dose of agrochemicals and their method of application, the species of cultivated plant, the nature of the soil and climatic conditions, for example length of time of exposure to light, temperature and amounts of precipitation. Thus, for example, it is known that cultivated plants which are to be protected from the adverse effect of undesirable plant growth may be damaged to a certain degree when an effective dose of herbicides from very different classes of substances, such as triazines, urea derivatives, carbamates, thiolcarbamates, halogenoacetanilides, halogenophenoxyacetic acids and other classes, are used. Various substances which are capable of specifically antagonising the harmful effect of a herbicide on the cultivated plants, i.e. of protecting the cultivated plants without at the same time noticeably influencing the herbicidal action on weeds to be combated, have already been proposed to solve this problem. However, it has been found that the antidotes proposed frequently have only a narrow field of use, i.e. a particular antidote is frequently suitable only for use with individual species of cultivated plants and/or for protecting the cultivated plants from individual herbicidal substances or classes of substances.

Thus, British Patent Specification 1,277,557 describes the treatment of seeds or shoots of wheat and sorghum with certain oxamic acid esters and amides for protection from attack by "ALACHLOR" (N-methoxymethyl-N-chloroacetyl-2,6-diethylaniline). German Offenlegungsschriften 1,952,910 and 2,245,471 and French Patent Specification 2,021,611 propose antidotes for treating cereal, maize and rice seeds to protect them from the harmful effect of herbicidally active thiolcarbamates. According to German Patent Specification 1,567,075 and U.S. Pat. No. 3,131,509, hydroxyaminoacetanilides and hydantoins are used for protecting cereal seeds from carbamates.

Direct pre- or post-emergent treatment of certain useful plants with antidotes, as antagonists of certain classes of herbicides, on a cultivated area is described in German Offenlegungsschriften 2,141,586 and 2,218,097 and in U.S. Pat. No. 3,867,444.

Furthermore, according to German Offenlegungsschrift 2,402,983, maize plants can be effectively protected from damage by chloroacetanilides by supplying the soil with an N-disubstituted dichloroacetamide as an antidote.

According to European Patent Application 11,047, alkoximinobenzyl cyanides in which the alkoxy group is substituted, inter alia, by an acetalised carbonyl group can also be used as agents for protecting cultivated plants from the harmful effect of herbicides of various classes of substances.

It has now been found that, surprisingly, a group of quinoline derivatives is outstandingly suitable for protecting cultivated plants from the harmful effects of agrochemicals, for example plant protection agents, especially herbicides. In the text which follows, these quinoline derivatives are therefore also called "antidotes" or "safeners". They also have a plant growth-regulating action and are particularly suitable for regulating the growth of dicotyledons, especially for increasing the yield of cultivated plants, especially soybean. Root growth and germination may also be promoted.

Quinoline derivatives which are suitable for protecting cultivated plants from the harmful effects of agrochemicals are those of the formula I

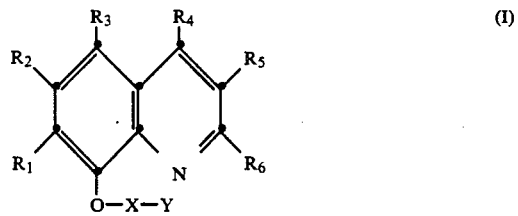

(I)

in which $R_1$, $R_2$ and $R_3$ independently of one another are hydrogen, halogen, nitro, cyano, alkyl or alkoxy, $R_4$, $R_5$ and $R_6$ independently of one another are hydrogen, halogen or alkyl, X is an aliphatic, acyclic, saturated hydrocarbon radical having 1 to 3 carbon atoms and Y is a carboxyl group or a salt thereof, a mercaptocarbonyl group or a salt thereof, a carboxylic acid ester group, a carboxylic acid thiolester group, an unsubstituted or substituted carboxylic acid amide group, a cyclised, unsubstituted or substituted derivative of a carboxylic acid amide group or a carboxylic acid hydrazide group, or X and Y together are an unsubstituted or substituted tetrahydrofuran-2-one ring, including acid addition salts and metal complexes thereof.

The compounds of the formula I in which X is —CH(CH$_3$)—, —(C$_2$H$_5$)— or —CH(A)—CH(E)—, A and E being as defined for formula I, or X and Y together are a tetrahydrofuran-2-one ring, they exist in the form of optical isomers. In the context of the present invention, the corresponding compounds of the formula I are to be understood as meaning both the optically pure isomers and the isomeric mixtures. Halogen is to be understood as meaning fluorine, chlorine, bromine or iodine, especially chlorine, bromine or iodine.

An alkyl or alkoxy group $R_1$, $R_2$, $R_3$, $R_4$, $R_5$ or $R_6$ can be straight-chain or branched, and advantageously contains 1 to 18, in particular 1 to 6 and preferably 1 to 3, carbon atoms.

An aliphatic, acyclic, saturated hydrocarbon radical X with 1 to 3 carbon atoms is, in particular, one of the following groups: $-CH_2-$, $-CH_2-CH_2-$, $-CH(CH_3)-$, $-CH_2-CH_2-CH_2-$, $-CH(C_2H_5)-$, $-C(CH_3)_2-$ or $-CH(A)-CH(E)-$, in which one of the symbols A and E is hydrogen and the other is a methyl group.

A carboxylic acid ester group or carboxylic acid thiolester group Y is a corresponding acid radical which is esterified, for example, by a substituted or unsubstituted aliphatic radical, or by a substituted or unsubstituted cycloaliphatic, aromatic or heterocyclic radical, which may be bonded via an aliphatic radical.

The preferred carboxylic acid ester radical is the radical $-COOR_7$ and the preferred carboxylic acid thiolester radical is the radical $-COSR_8$, in which $R_7$ and $R_8$ are as defined as follows: a substituted or unsubstituted alkyl, alkenyl, alkinyl, cycloalkyl, phenyl or naphthyl radical or a substituted or unsubstituted heterocyclic radical. The radicals $-COOR_7$ and $-COSR_8$ also include the free acids, in which $R_7$ and $R_8$ are hydrogen, and the salts thereof, in which $R_7$ and $R_8$ are cations. Particularly suitable salt-forming agents here are metals and organic nitrogen bases, especially quaternary ammonium bases. Metals which are suitable for salt formation are alkaline earth metals, such as magnesium or calcium, but especially alkali metals, such as lithium and, in particular, potassium and sodium. Transition metals, for example iron, nickel, cobalt, copper, zinc, chromium or manganese, are also suitable salt-forming agents. Examples of nitrogen bases which are suitable for salt formation are primary, secondary and tertiary aliphatic and aromatic amines, which may be hydroxylated on the hydrocarbon radical, such as methylamine, ethylamine, propylamine, isopropylamine, the four isomeric butylamines, dimethylamine, diethylamine, dipropylamine, diisopropylamine, di-n-butylamine, pyrrolidine, piperidine, morpholine, trimethylamine, triethylamine, tripropylamine, quinuclidine, pyridine, quinoline and isoquinoline, and methanolamine, ethanolamine, propanolamine, dimethanolamine, diethanolamine and triethanolamine. Organic nitrogen bases also include quaternary ammonium bases. Examples of quaternary ammonium bases are tetraalkylammonium cations in which the alkyl radicals independently of one another are straight-chain or branched $C_1$–$C_6$-alkyl groups, such as the tetramethylammonium cation, the tetraethylammonium cation or the trimethylethylammonium cation, and also the trimethylbenzylammonium cation, the triethylbenzylammonium cation and the trimethyl-2-hydroxyethylammonium cation. Particularly preferred salt-forming agents are the ammonium cation and trialkylammonium cations in which the alkyl radicals independently of one another are straight-chain or branched, unsubstituted or hydroxy-substituted $C_1$–$C_6$-alkyl groups, in particular $C_1$–$C_2$-alkyl groups, for example the trimethylammonium cation, the triethylammonium cation and the tri-(2-hydroxyethylene)-ammonium cation.

A carboxylic acid amide group Y is a corresponding amide radical, which can be unsubstituted or mono- or di-substituted on the nitrogen atom or in which the nitrogen atom is a constituent of a substituted or unsubstituted heterocyclic radical. Examples of substituents on the amide group are substituted or unsubstituted aliphatic radicals, which may be bonded via an oxygen atom, substituted or unsubstituted cycloaliphatic, aromatic or heterocyclic radicals, which may be bonded via an aliphatic radical, and unsubstituted or mono- or di-substituted amino groups.

The preferred carboxylic acid amide radical is the radical $-CONR_9R_{10}$, in which $R_9$ is hydrogen, a substituted or unsubstituted alkyl, alkenyl, alkinyl, cycloalkyl, phenyl or naphthyl radical, a substituted or unsubstituted heterocyclic radical or an alkoxy radical and $R_{10}$ is hydrogen, amino, mono- or di-substituted amino or a substituted or unsubstituted alkyl, alkenyl, cycloalkyl or phenyl radical, or $R_9$ and $R_{10}$, together with the nitrogen atom to which they are bonded, are a substituted or unsubstituted heterocyclic radical.

Examples of substituents on the organic radicals $R_7$, $R_8$, $R_8$, $R_9$ and $R_{10}$ are halogen, nitro, cyano, hydroxyl, alkyl, halogenoalkyl, alkoxy, which can be interrupted by one or more oxygen atoms, alkylthio, halogenoalkoxy, hydroxyalkoxy, which can be interrupted by one or more oxygen atoms, hydroxyalkylthio, alkoxycarbonyl, amino, alkylamino, dialkylamino, hydroxyalkylamino, di-(hydroxyalkyl)-amino, aminoalkylamino, cycloalkyl, substituted or unsubstituted phenyl, substituted or unsubstituted phenoxy and substituted or unsubstituted heterocyclic radicals.

Heterocyclic radicals are to be understood as preferably meaning 5- to 6-membered, saturated or unsaturated, substituted or unsubstituted monocyclic heterocyclic radicals having 1 to 3 hetero-atoms from the group comprising N, O and S, for example furan, tetrahydrofuran, tetrahydropyran, tetrahydropyrimidine, pyridine, piperidine, morpholine and imidazole.

Cycloalkyl radicals are to be understood particularly as meaning those having 3 to 8 carbon atoms, especially 3 to 6 carbon atoms.

Aliphatic acyclic radicals in the substituent Y can be straight-chain or branched and advantageously have not more than 18 carbon atoms. A lower number of carbon atoms is frequently advantageous, especially in composite substituents.

A cyclised derivative Y of a carboxylic acid amide group is, in particular, a substituted or unsubstituted oxazolin-2-yl radical, preferably an unsubstituted oxazolin-2-yl radical.

X and Y can together be a substituted or unsubstituted tetrahydrofuran-2-one ring, preferably an unsubstituted tetrahydrofuran-2-one ring, especially an unsubstituted tetrahydrofuran-2-on-3-yl ring.

Examples of salt-forming agents are organic and inorganic acids. Examples of organic acids are acetic acid, trichloroacetic acid, oxalic acid, benzenesulfonic acid and methanesulfonic acid. Examples of inorganic acids are hydrochloric acid, hydrobromic acid, hydriodic acid, sulfuric acid, phosphoric acid, phosphorous acid and nitric acid.

Examples of suitable metal complexing agents are elements of main groups 3 and 4, such as aluminium, tin and lead, and of sub-groups 1 to 8, for example chromium, manganese, iron, cobalt, nickel, zirconium, zinc, copper, silver and mercury. Sub-group elements of the 4th period are preferred.

Compounds of the formula I which belong to the groups of compounds listed below are particularly suitable for the use according to the invention.

a) Compounds of the formula I in which $R_1$, $R_2$, $R_3$, $R_4$, $R_5$, $R_6$ and X are as defined for formula I and Y is a substituted or unsubstituted oxazolin-2-yl radical, $-COOR_7$, $-COSR_8$ or $-CONR_9R_{10}$, in which $R_7$, $R_8$ and $R_9$ are hydrogen, substituted or unsubstituted alkyl, alkenyl, alkinyl, cycloalkyl, phenyl or naphthyl radicals or substituted or unsubstituted heterocyclic radicals, or $R_7$ and $R_8$ are cations, or $R_9$ is an alkoxy radical, and in which $R_{10}$ is hydrogen, amino, mono- or di-substituted amino or a substituted or unsubstituted alkyl, alkenyl, cycloalkyl or phenyl radical, or $R_9$ and $R_{10}$, together with the nitrogen atom to which they are bonded, are a substituted or unsubstituted heterocyclic radical, or X and Y together are a substituted or unsubstituted tetrahydrofuran-2-one ring, including acid addition salts and metal complexes thereof; preferred compounds of group a) are, as sub-group a/1, those in which $R_1$, $R_2$, $R_3$, $R_4$, $R_5$, $R_6$ and X are as defined for formula I and Y is a substituted or unsubstituted oxazolin-2-yl radical, —$COOR_7$, —$COSR_8$ or —$CONR_9R_{10}$, in which $R_7$ and $R_8$ independently of one another are hydrogen or cations; alkyl, which is unsubstituted or substituted by halogen, nitro, cyano, hydroxyl, alkoxy, which can be interrupted by one or more oxygen atoms, alkylthio, halogenoalkoxy, hydroxyalkoxy, which can be interrupted by one or more oxygen atoms, hydroxyalkylthio, alkoxycarbonyl, dialkylamino, cycloalkyl, substituted or unsubstituted phenyl, substituted or unsubstituted phenoxy or a substituted or unsubstituted heterocyclic radical; alkenyl, which is unsubstituted or substituted by halogen or substituted or unsubstituted phenyl; alkinyl, which is unsubstituted or substituted by halogen or hydroxyl; cycloalkyl, which is unsubstituted or substituted by halogen, alkyl or alkoxy; phenyl, which is unsubstituted or substituted by halogen, nitro, cyano, alkyl, alkoxy, alkoxycarbonyl or halogenoalkyl; naphthyl, which is unsubstituted or substituted by halogen, nitro or alkyl; or substituted or unsubstituted heterocyclic radicals; $R_9$ is hydrogen; alkyl, which is unsubstituted or substituted by halogen, cyano, hydroxyl, amino, alkylamino, dialkylamino, hydroxyalkylamino, di-(hydroxyalkyl)-amino, aminoalkylamino, alkoxy, alkoxycarbonyl, phenyl, which is unsubstituted or substituted by halogen, nitro, alkyl or alkoxy, cycloalkyl or a substituted or unsubstituted heterocyclic radical; alkoxy; alkenyl; cycloalkyl; phenyl, which is unsubstituted or substituted by halogen, nitro, cyano, alkyl, alkoxy or halogenoalkyl; naphthyl, which is unsubstituted or substituted by nitro or alkyl; or a substituted or unsubstituted heterocyclic radical; and $R_{10}$ is hydrogen; amino; dialkylamino; alkyl, which is unsubstituted or substituted by hydroxyl, cyano or alkoxy; alkenyl; cycloalkyl; or phenyl, or $R_9$ and $R_{10}$, together with the nitrogen atom to which they are bonded, are a substituted or unsubstituted heterocyclic radical, or X and Y together are a substituted or unsubstituted tetrahydrofuran-2-one ring, including acid sub-groups of compounds of group a/1 are those in which i) $R_1$, $R_2$, $R_3$, $R_4$, $R_5$, $R_6$ and X are as defined for formula I and Y is —$COOR_7$, in which $R_7$ is hydrogen, an alkali metal cation or a quaternary ammonium cation; $C_1$-$C_{18}$-alkyl; $C_1$-$C_{10}$-alkyl, which is substituted by halogen, nitro, cyano, hydroxyl, $C_1$-$C_8$-alkoxy, which can be interrupted by one or more oxygen atoms, $C_1$-$C_4$-alkylthio, $C_2$-$C_6$-halogenoalkoxy, $C_2$-$C_6$-hydroxyalkoxy, which can be interrupted by one or more oxygen atoms, $C_2$-$C_6$-hydroxyalkylthio, $C_1$-$C_4$-alkoxycarbonyl, $C_2$-$C_{12}$-dialkylamino or substituted or unsubstituted phenoxy; $C_1$-$C_6$-alkyl, which is substituted by phenyl, which is unsubstituted or substituted by halogen, nitro, $C_1$-$C_3$-alkyl or $C_1$-$C_3$-alkoxy, $C_3$-$C_6$-cycloalkyl or a substituted or unsubstituted, saturated or unsaturated heterocyclic radical having 1 to 3 hetero-atoms; $C_3$-$C_{10}$-alkenyl, which is unsubstituted of substituted by halogen or substituted or unsubstituted phenyl; $C_3$-$C_6$-alkinyl, which is unsubstituted or substituted by halogen or hydroxyl; $C_3$-$C_8$-cycloalkyl, which is unsubstituted or substituted by halogen, $C_1$-$C_3$-alkyl or $C_1$-$C_3$-alkoxy; phenyl, which is unsubstituted or substituted by halogen, nitro, cyano, $C_1$-$C_4$-alkyl, $C_1$-$C_4$-alkoxy, $C_1$-$C_4$-alkoxycarbonyl or $C_1$-$C_2$-halogenoalkyl; naphthyl, which is unsubstituted or substituted by halogen, nitro or $C_1$-$C_3$-alkyl; or a 5- or 6-membered, saturated or unsaturated, substituted or unsubstituted heterocyclic ring having 1 to 3 hetero-atoms from the group comprising N, O, and S, and, of these compounds, especially those in which $R_1$, $R_2$, $R_3$, $R_4$, $R_5$, $R_6$ and X are as defined for formula I and Y is —$COOR_7$, in which $R_7$ is hydrogen, an alkali metal cation or a quaternary ammonium cation chosen from the group comprising the ammonium cation and the trimethyl-, triethyl- and tri-(2-hydroxyethylene)-ammonium cations; $C_1$-$C_{18}$-alkyl; $C_1$-$C_{10}$-alkyl, which is substituted by 1 or 2 hydroxyl groups; $C_1$-$C_4$-alkyl, which is substituted by 1 to 3 chlorine or bromine atoms, a nitro group, a cyano group, a $C_1$-$C_4$-alkoxy group, a $C_2$-$C_8$-alkoxy group, which is interrupted by 1 or 2 oxygen atoms, a hydroxy-$C_1$-$C_4$-alkoxy group, a hydroxy-$C_2$-$C_6$-alkoxy group, which is interrupted by 1 or 2 oxygen atoms, a $C_1$-$C_4$-alkoxycarbonyl group, a di-($C_1$-$C_4$-alkyl)-amino group, a phenyl radical, which is unsubstituted or substituted by chlorine or methoxy, a cyclohexyl radical or a furan, tetrahydrofuran, tetrahydropyran, pyridino, piperidino or morpholino radical; $C_3$-$C_{10}$-alkenyl; $C_2$-$C_4$-alkinyl, which is unsubstituted or substituted by a hydroxyl group; cyclohexyl, which is unsubstituted or substituted by 1 or 2 methyl groups; phenyl, which is unsubstituted or substituted by 1 or 2 substituents from the group comprising chlorine, nitro, $C_1$-$C_4$-alkyl and methoxy; naphthyl; or pyridine;

ii) $R_1$, $R_2$, $R_3$, $R_4$, $R_5$, $R_6$ and X are as defined for formula I and Y is —$COSR_8$, in which $R_8$ is hydrogen; $C_1$-$C_{18}$-alkyl; $C_1$-$C_{10}$-alkyl, which is substituted by halogen, nitro, cyano, hydroxyl, $C_1$-$C_8$-alkoxy, which can be interrupted by one or more oxygen atoms, $C_1$-$C_4$-alkylthio, $C_2$-$C_6$-halogenoalkoxy, $C_2$-$C_6$-hydroxyalkoxy, which can be interrupted by one or more oxygen atoms, $C_2$-$C_6$-hydroxyalkylthio, $C_1$-$C_4$-alkoxycarbonyl, $C_2$-$C_{12}$-dialkylamino or substituted or unsubstituted phenoxy; $C_1$-$C_6$-alkyl, which is substituted by phenyl, which is unsubstituted or substituted by halogen, nitro, $C_1$-$C_3$-alkyl or $C_1$-$C_3$-alkoxy, $C_3$-$C_6$-cycloalkyl or a substituted or unsubstituted, saturated or unsaturated heterocyclic radical having 1 to 3 hetero-atoms; $C_3$-$C_{10}$-alkenyl, which is unsubstituted or substituted by halogen or substituted or unsubstituted phenyl; $C_3$-$C_6$-alkinyl, which is unsubstituted or substituted by halogen or hydroxyl; $C_3$-$C_8$-cycloalkyl, which is unsubstituted or substituted by halogen, $C_1$-$C_3$-alkyl or $C_1$-$C_3$-alkoxy; phenyl, which is unsubstituted or substituted by halogen, nitro, cyano, $C_1$-$C_4$-alkyl, $C_1$-$C_4$-alkoxy, $C_1$-$C_4$-alkoxycarbonyl or $C_1$-$C_2$-halogenoalkyl; naphthyl, which is unsubstituted or substituted by halogen, nitro or $C_1$-$C_3$-alkyl; or a 5- or 6-membered, saturated or unsaturated, substituted or unsubstituted heterocyclic ring having 1 to 3 hetero-atoms from the group comprising N, O, and S, and, of these compounds, especially those in which $R_1$, $R_2$, $R_3$, $R_4$, $R_5$, $R_6$ and X are as defined for formula I and Y is —$COSR_8$, in which $R_8$ is $C_1$-$C_{12}$-alkyl; $C_1$-$C_4$-alkyt, which is substituted by a $C_1$-$C_4$-alkoxycarbonyl group;

or phenyl, which unsubstituted or substituted by a chlorine atom;

iii) $R_1$, $R_2$, $R_3$, $R_4$, $R_5$, $R_6$ and X are as defined for formula I and Y is —$CONR_9R_{10}$, in which $R_9$ is hydrogen; $C_1$–$C_{18}$ alkyl, $C_2$–$C_8$-alkyl, which is substituted by amino; $C_2$–$C_6$-alkyl, which is substituted by halogen, hydroxyl, $C_1$–$C_6$-alkylamino, $C_2$–$C_8$-dialkylamino, $C_2$–$C_6$-hydroxyalkylamino, $C_2$–$C_6$-di-(hydroxyalkyl)-amino, $C_2$–$C_6$-aminoalkylamino or $C_1$–$C_4$-alkoxycarbonyl; $C_1$–$C_4$-alkyl, which is substituted by cyano, $C_1$–$C_4$-alkoxy, phenyl, which is unsubstituted or substituted by halogen, nitro, $C_1$–$C_3$-alkyl or $C_1$–$C_3$-alkoxy, $C_3$–$C_6$-cycloalkyl or a 5- or 6-membered, saturated or unsaturated, substituted or unsubstituted heterocyclic ring having 1 to 3 hetero-atoms from the group comprising N, O and S; $C_1$–$C_3$-alkoxy; $C_3$–$C_6$-alkenyl; $C_3$–$C_8$-cycloalkyl; phenyl, which is unsubstituted or substituted by halogen, nitro, cyano, $C_1$–$C_4$-alkyl, $C_1$–$C_4$-alkoxy or $C_1$–$C_2$-halogenoalkyl; or naphthyl, which is unsubstituted or substituted by nitro or methyl; and $R_{10}$ is hydrogen; amino; $C_2$–$C_4$-dialkylamino; $C_1$–$C_6$-alkyl; $C_1$–$C_4$-alkyl, which is substituted by hydroxyl or cyano; $C_2$–$C_6$-alkoxyalkyl; $C_3$–$C_6$-alkenyl; $C_3$–$C_6$-cycloalkyl; or phenyl; or in which $R_9$ and $R_{10}$, together with the nitrogen atom to which they are bonded, are a 5- or 6-membered, saturated or unsaturated, substituted or unsubstituted heterocyclic ring, which can also contain 1 or 2 other hetero-atoms from the group comprising N, O and S, and of these compounds especially those in which $R_1$, $R_2$, $R_3$, $R_4$, $R_5$, $R_6$ and X are as defined for formula I and Y is —$CONR_9R_{10}$, in which $R_9$ is hydrogen; $C_1$–$C_{18}$-alkyl; $C_2$–$C_8$-alkyl, which is substituted by an amino group; $C_2$–$C_6$-alkyl, which is substituted by a hydroxyl group; $C_2$–$C_4$-alkyl, which is substituted by a chlorine or bromine atom, a $C_1$–$C_4$-alkylamino group, a di-($C_1$–$C_4$-alkyl)-amino group, a $C_1$–$C_4$-hydroxyalkylamino group, a di-($C_1$–$C_3$-hydroxyalkyl)-amino group, a $C_1$–$C_4$-alkoxy group or a $C_1$–$C_4$-alkoxycarbonyl group; $C_1$–$C_4$-alkyl, which is substituted by a cyano group, a phenyl radical, which is unsubstituted or substituted by chlorine, or a furanyl, tetrahydrofuranyl, piperidino or morpholino radical; $C_1$–$C_3$-alkoxy; $C_2$–$C_4$-alkenyl; cyclohexyl, which is unsubstituted or substituted by a methyl group; or phenyl, which is unsubstituted or substituted by 1 or 2 substituents from the group comprising chlorine, nitro, cyano, methyl, ethyl, methoxy and trifluoromethyl, and $R_{10}$ is hydrogen; $C_1$–$C_6$-alkyl; $C_1$–$C_4$-alkyl, which is substituted by a hydroxyl group or a cyano group; $C_2$–$C_4$-alkoxyalkyl; $C_2$–$C_4$-alkenyl; cyclohexyl; or phenyl, or $R_9$ and $R_{10}$, together with the nitrogen atom to which they are bonded, are a piperidino, tetrahydropyrimidino, morpholino or imidazolyl radical which is unsubstituted or substituted by 1 or 2 methyl groups;

iv) $R_1$, $R_2$, $R_3$, $R_4$, $R_5$, $R_6$ and X are as defined for formula I and Y is a substituted or unsubstituted oxazolin-2-yl radical, and of these compounds, especially those in which $R_1$, $R_2$, $R_3$, $R_4$, $R_5$, $R_6$ and X are as defined for formula I and Y is an unsubstituted oxazolin-2-yl radical; and v) $R_1$, $R_2$, $R_3$, $R_4$, $R_5$ and $R_6$ are as defined for formula I and X and Y together are a substituted or unsubstituted tetrahydrofuran-2-one ring, and of these compounds, especially those in which $R_1$, $R_2$, $R_3$, $R_4$, $R_5$ and $R_6$ are as defined for formula I and X and Y together are an unsubstituted tetrahydrofuran-2-one ring, in particular an unsubstituted tetrahydrofuran-2-on-3-yl ring;

b) compounds of the formula I in which $R_1$, $R_2$, $R_3$, $R_4$, $R_5$, $R_6$ and Y are as defined for formula I and X is —$CH_2$—;

c) compounds of the formula I in which $R_1$, $R_2$, $R_3$, $R_4$, $R_5$, $R_6$ and Y are as defined for formula I and X is —$CH_2$—$CH_2$;

d) compounds of the formula I in which $R_1$, $R_2$, $R_3$, $R_4$, $R_5$, $R_6$ and Y are as defined for formula I and X is —$CH(CH_3)$—;

e) compounds of the formula I in which $R_1$, $R_2$, $R_3$, $R_4$, $R_5$, $R_6$ and Y are as defined for formula I and X is —$CH(A)$—$CH(E)$—, in which one of the symbols A and E is hydrogen and the other is a methyl group;

f) compounds of the formula I in which $R_1$, $R_2$, $R_3$, $R_4$, $R_5$, $R_6$ and Y are as defined for formula I and X is —$CH_2$—$CH_2$—$CH_2$—;

g) compounds of the formula I in which $R_1$, $R_2$, $R_3$, $R_4$, $R_5$, $R_6$ and Y are as defined for formula I and X is —$CH(C_2H_5)$—;

h) compounds of the formula I in which $R_1$, $R_2$, $R_3$, $R_4$, $R_5$ $R_6$ and Y are as defined for formula I and X is —$C(CH_3)_2$—;

i) compounds of the formula I in which $R_1$, $R_2$ and $R_3$ independently of one another are hydrogen, halogen, nitro or $C_1$–$C_3$-alkyl, $R_4$, $R_5$ and $R_6$ independently of one another are hydrogen or $C_1$–$C_3$-alkyl and X and Y are as defined for formula I;

k) compounds of the formula I in which $R_1$ is hydrogen or halogen, $R_2$ is hydrogen, $R_3$ is hydrogen, halogen, nitro or $C_1$–$C_3$-alkyl, $R_4$ is hydrogen, $R_5$ is hydrogen, $R_6$ is hydrogen or $C_1$–$C_3$-alkyl and X and Y are as defined for formula I;

l) compounds of the formula I in which $R_1$ is hydrogen, chlorine, iodine or bromine, $R_2$ is hydrogen, $R_3$ is hydrogen, chlorine, iodine, bromine, nitro, methyl or ethyl, $R_4$ is hydrogen, $R_5$ is hydrogen, $R_6$ is hydrogen or methyl and X and Y are as defined for formula I;

m) compounds of the formula I in which $R_1$, $R_2$ and $R_3$ independently of one another are hydrogen, halogen, nitro or $C_1$–$C_3$-alkyl, $R_4$, $R_5$ and $R_6$ independently of one another are hydrogen or $C_1$–$C_3$-alkyl, X is as defined for formula I and Y is a substituted or unsubstituted oxazolin-2-yl radical, —$COOR_7$, —$COSR_8$ or —$CONR_9R_{10}$, in which $R_7$ is hydrogen, an alkali metal cation or a quaternary ammonium cation; $C_1$–$C_{18}$-alkyl; $C_1$–$C_{10}$-alkyl, which is substituted by halogen, nitro, cyano, hydroxyl, $C_1$–$C_8$-alkoxy, which can be interrupted by one or more oxygen atoms, $C_1$–$C_4$-alkylthio, $C_2$–$C_6$-halogenoalkoxy, $C_2$–$C_6$-hydroxyalkoxy, which can be interrupted by one or more oxygen atoms, $C_2$–$C_6$-hydroxyalkylthio, $C_1$–$C_4$-alkoxycarbonyl, $C_2$–$C_{12}$-dialkylamino or substituted or unsubstituted phenoxy; $C_1$–$C_6$-alkyl, which is substituted by phenyl, which is unsubstituted or substituted by halogen, nitro, $C_1$–$C_3$-alkyl or $C_1$–$C_3$-alkoxy, $C_3$–$C_6$-cycloalkyl or a substituted or unsubstituted, saturated or unsaturated heterocyclic radical having 1 to 3 hetero-atoms; $C_3$–$C_{10}$-alkenyl, which is unsubstituted or substituted by halogen or substituted or unsubstituted phenyl; $C_3$–$C_6$-alkinyl, which is unsubstituted or substituted by halogen or hydroxyl; $C_3$–$C_8$-cycloalkyl, which is unsubstituted or substituted by halogen, $C_1$–$C_3$-alkyl or $C_1$–$C_3$-alkoxy; phenyl, which is unsubstituted or substituted by halogen, nitro, cyano, $C_1$–$C_4$-alkyl, $C_1$–$C_4$-alkoxy, $C_1$–$C_4$-alkoxycarbonyl or $C_1$–$C_2$-halogenoalkyl; naphthyl, which is unsubstituted or substituted by halogen, nitro or $C_1$–$C_3$-alkyl; or a 5- or 6-membered, saturated or unsaturated, substituted or unsubstituted heterocyclic ring having 1 to 3 hetero-atoms from the group comprising N, O and S, $R_8$ is hydrogen; $C_1-C_{18}$-alkyl; $C_1-C_{10}$-alkyl, which is substituted by halogen, nitro, cyano, hydroxyl, $C_1-C_8$-alkoxy, which can be interrupted by one or more oxygen atoms, $C_1-C_4$-alkylthio, $C_2-C_6$-halogenoalkoxy, $C_2-C_6$-hydroxyalkoxy, which can be interrupted by one or more oxygen atoms, $C_2-C_6$-hydroxyalkylthio, $C_1-C_4$-alkoxycarbonyl, $C_2-C_{12}$-dialkylamino or substituted or unsubstituted phenoxy; $C_1-C_6$-alkyl, which is substituted by phenyl, which is unsubstituted or substituted by halogen, nitro, $C_1-C_3$-alkyl or $C_1-C_3$-alkoxy, $C_3-C_6$-cycloalkyl or a substituted or unsubstituted, saturated or unsaturated heterocyclic radical having 1 to 3 hetero-atoms; $C_3-C_{10}$-alkenyl, which is unsubstituted or substituted by halogen or substituted or unsubstituted phenyl; $C_3-C_6$-alkinyl, which is unsubstituted or substituted by halogen or hydroxyl; $C_3-C_8$-cycloalkyl, which is unsubstituted or substituted by halogen, $C_1-C_3$-alkyl or $C_1-C_3$-alkoxy; phenyl, which is unsubstituted or substituted by halogen, nitro, cyano, $C_1-C_4$-alkyl, $C_1-C_4$-alkoxy, $C_1-C_4$-alkoxycarbonyl or $C_1-C_2$-halogenoalkyl; naphthyl, which is unsubstituted or substituted by halogen, nitro or $C_1-C_3$-alkyl; or a 5- or 6-membered, saturated or unsaturated, substituted or unsubstituted heterocyclic ring having 1 to 3 hetero-atoms from the group comprising N, O and S, in which $R_9$ is hydrogen; $C_1-C_{18}$ alkyl; $C_2-C_8$-alkyl, which is substituted by amino; $C_2-C_6$-alkyl, which is substituted by halogen, hydroxyl, $C_1-C_6$-alkylamino, $C_2-C_8$-dialkylamino, $C_2-C_6$-hydroxyalkylamino, $C_2-C_6$-di-(hydroxyalkyl)-amino, $C_2-C_6$-aminoalkylamino or $C_1-C_4$-alkoxycarbonyl; $C_1-C_4$-alkyl, which is substituted by cyano, $C_1-C_4$-alkoxy, phenyl, which is unsubstituted or substituted by halogen, nitro, $C_1-C_3$-alkyl or $C_1-C_3$-alkoxy, $C_3-C_6$-cycloalkyl or a 5- or 6-membered, saturated or unsaturated, substituted or unsubstituted heterocyclic ring having 1 to 3 hetero-atoms from the group comprising N, O and S; $C_1-C_3$-alkoxy; $C_3-C_6$-alkenyl; $C_3-C_8$-cycloalkyl; phenyl, which is unsubstituted or substituted by halogen, nitro, cyano, $C_1-C_4$-alkyl, $C_1-C_4$-alkoxy or $C_1-C_2$-halogenoalkyl; or naphthyl, which is unsubstituted or substituted by nitro or methyl; and $R_{10}$ is hydrogen; amino; $C_2-C_4$-dialkylamino, $C_1-C_6$-alkyl; $C_1-C_4$-alkyl, which is substituted by hydroxyl or cyano; $C_2-C_6$-alkoxyalkyl; $C_3-C_6$-alkenyl; $C_3-C_6$-cycloalkyl; or phenyl; or in which $R_9$ and $R_{10}$, together with the nitrogen atom to which they are bonded, are a 5- or 6-membered, saturated or unsaturated, substituted or unsubstituted heterocyclic ring, which can also contain 1 or 2 other hetero-atoms from the group comprising N, O and S, or X and Y together are a substituted or unsubstituted tetrahydrofuran-2-one ring.

n) compounds of the formula I in which $R_1$ is hydrogen, chlorine, iodine or bromine, $R_2$ is hydrogen, $R_3$ is hydrogen, chlorine, iodine, bromine, nitro, methyl or ethyl, $R_4$ is hydrogen, $R_5$ is hydrogen, $R_6$ is hydrogen or methyl, X is as defined for formula I and Y is an unsubstituted oxazolin-2-yl radical, —$COOR_7$, —$COSR_8$ or —$CONR_9R_{10}$, in which $R_7$ is hydrogen, an alkali metal cation or a quaternary ammonium cation chosen from the group comprising the ammonium cation and the trimethyl-, triethyl- and tri-(2-hydroxyethylene)-ammonium cations; $C_1-C_{18}$-alkyl; $C_1-C_{10}$-alkyl, which is substituted by 1 or 2 hydroxy groups; $C_1-C_4$-alkyl, which is substituted by 1 to 3 chlorine or bromine atoms, a nitro group, a cyano group, a $C_1-C_4$-alkoxy group, a $C_2-C_8$-alkoxy group, which is interrupted by 1 or 2 oxygen atoms, a hydroxy-$C_1-C_4$-alkoxy group, a hydroxy-$C_2-C_6$-alkoxy group, which is interrupted by 1 or 2 oxygen atoms, a $C_1-C_4$-alkoxycarbonyl group, a di-($C_1-C_4$-alkyl)-amino group, a phenyl radical, which is unsubstituted or substituted by chlorine or methoxy, a cyclohexyl radical or a furan, tetrahydrofuran, tetrahydropyran, pyridino, piperidino or morpholino radical; $C_3-C_{10}$-alkenyl; $C_2-C_4$-alkinyl, which is unsubstituted or substituted by a hydroxyl group; cyclohexyl, which is unsubstituted or substituted by 1 or 2 methyl groups; phenyl, which is unsubstituted or substituted by 1 or 2 substituents from the group comprising chlorine, nitro, $C_1-C_4$-alkyl and methoxy; naphthyl; or pyridine, $R_8$ is $C_1-C_{12}$-alkyl; $C_1-C_4$-alkyl, which is substituted by a $C_1-C_4$-alkoxycarbonyl group; or phenyl, which is unsubstituted or substituted by a chlorine atom; $R_9$ is hydrogen; $C_1-C_{18}$-alkyl; $C_2-C_8$-alkyl, which is substituted by an amino group; $C_2-C_6$-alkyl, which is substituted by a hydroxyl group; $C_2-C_4$-alkyl, which is substituted by a chlorine or bromine atom, a $C_1-C_4$-alkylamino group, a di-($C_1-C_4$-alkyl)-amino group, a $C_1-C_4$-hydroxyalkylamino group, a di-($C_1-C_3$-hydroxyalkyl)-amino group, a $C_1-C_4$-alkoxy group or a $C_1-C_4$-alkoxycarbonyl group; $C_1-C_4$-alkyl, which is substituted by a cyano group, a phenyl radical, which is unsubstituted or substituted by chlorine, or a furanyl, tetrahydrofuranyl, piperidino or morpholino radical; $C_1-C_3$-alkoxy; $C_2-C_4$-alkenyl; cyclohexyl, which is unsubstituted or substituted by a methyl group; or phenyl, which is unsubstituted or substituted by 1 or 2 substituents from the group comprising chlorine, nitro, cyano, methyl, ethyl, methoxy and trifluoromethyl, and $R_{10}$ is hydrogen; $C_1-C_6$-alkyl; $C_1-C_4$-alkyl, which is substituted by a hydroxyl group or a cyano group; $C_2-C_4$-alkoxyalkyl; $C_2-C_4$-alkenyl; cyclohexyl; or phenyl, or $R_9$ and $R_{10}$, together with the nitrogen atom to which they are bonded, are a piperidino, tetrahydropyrimidino, morpholino or imidazolyl radical which is unsubstituted or substituted by 1 or 2 methyl groups, or X and Y together are an unsubstituted tetrahydrofuran-2-on-3-yl ring;

o) compounds of the above group m) in which X is —$CH_2$—, with the proviso that if, at the same time, $R_1$ is hydrogen, chlorine, bromine or iodine, $R_2$ is hydrogen, nitro or methyl, $R_3$ is hydrogen, chlorine, bromine, nitro, methyl or ethyl, $R_4$ and $R_5$ are hydrogen, $R_6$ is hydrogen or methyl and Y is —$COOR_7$ or —$CONR_9R_{10}$, i) $R_7$ is not hydrogen or $C_1-C_4$-alkyl which is unsubstituted or substituted by diethylamino, and ii) $R_9$ is not hydrogen, $C_1-C_4$-alkyl, allyl or phenyl which is unsubstituted or substituted by p-chloro, if $R_{10}$ is hydrogen, amino, $C_1-C_4$-alkyl, allyl or phenyl, and iii) $R_9$ and $R_{10}$, together with the nitrogen atom to which they are bonded, are not a morpholine ring;

p) compounds of the above group n) in which X is —$CH_2$—, with the proviso that if, at the same time, $R_1$ is hydrogen, chlorine, iodine or bromine, $R_2$ is hydrogen, $R_3$ is hydrogen, chlorine, bromine, nitro, methyl or ethyl, $R_4$ and $R_5$ are hydrogen, $R_6$ is hydrogen or methyl and Y is —$COOR_7$ or —$CONR_9R_{10}$, i) $R_7$ is not hydrogen or $C_1-C_4$-alkyl which is unsubstituted or substituted by diethylamino, and ii) $R_9$ is not hydrogen, $C_1-C_4$-alkyl, allyl or phenyl which is unsubstituted or substituted by p-chloro, if $R_{10}$ is hydrogen, $C_1-C_4$-alkyl, allyl or phenyl, and iii) $R_9$ and $R_{10}$, together with the nitrogen atom to which they are bonded, are not a morpholine ring;

q) compounds of the above group m), in which X is —CH$_2$—CH$_2$—, with the proviso that if, at the same time, R$_1$, R$_2$, R$_3$, R$_4$, R$_5$ and R$_6$ are hydrogen and Y is —COOR$_7$, R$_7$ is not hydrogen;

r) compounds of the above group n) in which X is —CH$_2$—CH$_2$—, with the proviso that if R$_1$, R$_2$, R$_3$, R$_4$, R$_5$ and R$_6$ are hydrogen and Y is —COOR$_7$, R$_7$ is not hydrogen;

s) compounds of the above group m) in which X is —CH(CH$_3$)—, with the proviso that if R$_1$ is hydrogen or chlorine, R$_2$ is hydrogen, R$_3$ is hydrogen or chlorine, R$_4$ and R$_5$ are hydrogen R$_6$ is hydrogen or methyl and Y is —COOR$_7$ or —CONR$_9$R$_{10}$, i) R$_7$ is not ethoxy, and ii) R$_9$ is not hydrogen, ethyl, sec.-butyl or allyl, if R$_{10}$ is hydrogen, ethyl, sec.-butyl or allyl, and iii) R$_9$ and R$_{10}$, together with the nitrogen atom to which they are bonded, are not a pyrrolidino ring;

t) compounds of the above group n) in which X is —CH(CH$_3$)—, with the proviso that if, at the same time, R$_1$ is hydrogen or chlorine, R$_2$ is hydrogen, R$_3$ is hydrogen or chlorine, R$_4$ and R$_5$ are hydrogen, R$_6$ is hydrogen or methyl and Y is —COOR$_7$ or —CONR$_9$R$_{10}$, i) R$_7$ is not ethyl and ii) R$_9$ is not hydrogen, ethyl, sec.-butyl or allyl, if R$_{10}$ is hydrogen, ethyl, sec.-butyl or allyl;

u) compounds of the above group m) in which X is —CH(A)—CH(E)—, in which one of the symbols A and E is hydrogen and the other is a methyl group;

v) compounds of the above group n) in which X is —CH(A)—CH(E)—, in which one of the symbols A and E is hydrogen and the other is a methyl group;

w) compounds of the above group m) in which X is —CH$_2$—CH$_2$—CH$_2$—, with the proviso that if at the same time, R$_1$, R$_2$, R$_3$, R$_4$, R$_5$ and R$_6$ are hydrogen and Y is —COOR$_7$ or —CONR$_9$R$_{10}$, R$_7$ is not hydrogen, methyl or ethyl and R$_9$ and R$_{10}$ are not both ethyl;

x) compounds of the above group n) in which X is —CH$_2$—CH$_2$—CH$_2$—, with the proviso that if, at the same time, R$_1$, R$_2$, R$_3$, R$_4$, R$_5$ and R$_6$ are hydrogen and Y is —COOR$_7$ or —CONR$_9$R$_{10}$, R$_7$ is not hydrogen, methyl or ethyl and R$_9$ and R$_{10}$ are not both ethyl;

y) compounds of the above group m) in which X is —CH(C$_2$H$_5$)—;

z) compounds of the above group n) in which X is —CH(C$_2$H$_5$)—;

z$^1$) compounds of the above group m) in which X is —C(CH$_3$)$_2$—;

z$^2$) compounds of the above group n) in which X is —C(CH$_3$)$_2$—;

z$^3$) compounds of the above group m) in which X and Y together are a substituted or unsubstituted tetrahydrofuran-2-one ring;

z$^4$) compound of the above group n) in which X and Y together are a substituted or unsubstituted tetrahydrofuran-2-one ring.

The quinoline derivatives of the formula I have to an outstanding degree the property of protecting cultivated plants from the harmful effects of agrochemicals. Examples of agrochemicals are defoliants, desiccants, agents for protection from frost damage and plant protection agents, for example insecticides, fungicides, bactericides, nematocides and, in particular, herbicides. The agrochemicals can belong to various classes of substances. For example, herbicides can belong to one of the following classes of substances: triazines and triazinones; ureas, for example 1-(benzothiazol-2-yl)-1,3-dimethylurea ("methabenzthiazuron") or, in particular, phenylureas, especially 3-(4-isopropylphenyl)-1,1-dimethylurea ("isoproturon"), or sulfonylureas; carbamates and thiocarbamates; halogenoacetanilides, in particular chloroacetanilides; chloroacetamides; halogenophenoxyacetic acid esters; diphenyl ethers, for example substituted phenoxyphenoxyacetic acid esters and amides and substituted phenoxyphenoxypropionic acid esters and amides; substituted pyridyloxyphenoxyacetic acid esters and amides and substituted pyridyloxyphenoxypropionic acid esters and amides, in particular 2-propinyl 2-[4-(3,5-dichloropyridyl-2-oxy)-phenoxy]-propionate and n-butyl 2-[4-(5-trifluoromethylpyridyl-2-oxy)-phenoxy]-propionate; benzoic acid derivatives; nitroanilines; oxadiazolones; phosphates; and pyrazoles.

The following substances are specific examples:

triazines and triazinones: 2,4-bis(isopropylamino)-6-methylthio-1,3,5-triazine ("prometryn"), 2,4-bis(ethylamino)-6-methylthio-1,3,5-triazine ("simetryne"), 2-(1',2'-dimethylpropylamino)-4-ethylamino-6-methylthio-1,3,5-triazine ("dimethametryne"), 4-amino-6-tert.-butyl-4,5-dihydro-3-methylthio-1,2,4-triazin-5-one ("metribuzin"), 2-chloro-4- 1-ethylamino-6-isopropylamino-1,3,5-triazine ("atrazine"), 2-chloro-4,6-bis(ethylamino)-1,3,5-triazine ("simazine"), 2-tert.-butylamino-4-chloro-6-ethylamino-1,3,5-triazine ("terbutylazine"), 2-tert.-butylamino-4-ethylamino-6-methoxy-1,3,5-triazine ("terbumeton"), 2-tert.-butylamino-4-ethylamino- 6-methylthio-1,3,5-triazine ("terbutryn") and 2-ethylamino-4-isopropylamino-6-methylthio-1,3,5-triazine ("ametryn");

ureas: 1-(benzothiazol-2-yl)-1,3-dimethylurea; phenylureas, for example 3-(3-chloro-p-tolyl)-1,1-dimethylurea ("chlortoluron"), 1,1-dimethyl-3- $\alpha\alpha\alpha$-trifluoro-m-tolyl)-urea ("fluometuron"), 3-(4-bromo-3-chlorophenyl)-1-methoxy-1-methylurea ("chlorbromuron"), 3-(4-bromophenyl)-1-methoxy-1-methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron") and 3-(3-chloro-4-methoxyphenyl)-1,1-dimethylurea ("metoxuron"); sulfonylureas, for example N-(2-chlorophenylsulfonyl)-N'-(4-methoxy-6-methyl-1,3,5-triazin-2-yl)urea, N-(2-methoxycarbonylphenylsulfonyl)-N'-(4,6-dimethylpyrimidin-2-yl)-urea, N-(2,5-dichlorophenylsulfonyl)-N'-(4,6-dimethoxypyrimidin-2-yl)-urea and N-[2-(2-butenyloxy)phenylsulfonyl]-N'-(4-methoxy-6-methyl-1,3,5-triazin-2-yl)urea, and the sulfonylureas mentioned in European Patent Publications 44,808 and 44,809;

carbamates and thiocarbamates: N-(3',4'-dichlorophenyl)propionanilide ("propanil"), S-4-chlorobenzyl diethyl-thiocarbamate ("benthiocarb"), S-ethyl N,N-hexamethylene-thiocarbamate ("molinate"), S-ethyl di-propyl-thiocarbamate ("EPTC"), S-benzyl N,N-di-sec.-butyl-thiocarbamate, S-(2,3-dichloroallyl) di-isopropyl-thiocarbamate ("di-allate"), 1-(propylthiocarbonyl)-decahydro-quinaldine and S-ethyl diisobutyl-thiocarbamate ("butylate");

chloroacetanilides: 2-chloro-2',6'-diethyl-N-(2''-n-propoxyethyl)-acetanilide ("propalochlor"), 2-chloro-6'-ethyl-N-(2''-methoxy-1''-methylethyl)-acet-o-toluidide ("metolachlor"), 2-chloro-2',6'-diethyl-N-(butoxymethyl)-acetanilide ("butachlor"), 2-chloro-6'-ethyl-N-(ethoxymethyl)-acet-o-toluidide ("acetochlor"), 2-chloro-6'-ethyl-N-(2''-propoxy-1''-methylethyl)-acet-o- toluidide, 2-chloro-2',6'-dimethyl-N-(2''-methoxy-1''-methylethyl)-acetanilide, 2-chloro-2',6'-dimethyl-N-(2''-methoxyethyl)-acetanilide ("dimethachlor"), 2-chloro-2',6'-diethyl-N-(pyrazol-1-ylmethyl)-acetanilide, 2-chloro-6'-ethyl-N-(pyrazol-1-ylmethyl)-acet-o-toluidide, 2-chloro-6'-ethyl-N-(3,5-dimethyl-pyrazol-1-ylmethyl)-acet-o-toluidide, 2-chloro-6'-ethyl-N-(2''-butoxy-1''-methylethyl)-acet-o-toluidide ("metazolachlor"), 2-chloro-6'-ethyl-N-(2''-butoxyl-1''-(methylethyl)-acet-o-toluidide and 2-chloro-2'-trimethylsilyl-N-(butoxymethyl)-acetanilide;

chloroacetamides: N-[1-isopropyl-2-methylprop-1-en-1-yl]-N-(2'-methoxyethyl)-chloroacetamide;

diphenyl ethers and nitrodiphenyl ethers: 2,4-dichlorophenyl 4'-nitrophenyl ether ("nitrofen"), 2-chloro-1-(3'-ethoxy-4'-nitrophenoxy)-4-trifluoromethyl-benzene ("oxyfluorfen"), 2',4'-dichlorophenyl-3-methoxy-4-nitrophenyl ether ("chlormethoxynil"), methyl 2-[4'-(2'',4''-dichlorophenoxy)-phenoxy)-propionate, N-(2'-phenoxyethyl)-2-[5'-(2''-chloro-4''-trifluoromethylphenoxy)-phenoxy]-propionamide, 2-methoxyethyl 2-[2-nitro-5-(2-chloro-4-trifluoromethylphenoxy)-phenoxy]-propionate and 2-chloro-4-trifluoromethylphenyl 3'-oxazolin-2'-yl-4'-nitrophenyl ether;

benzoic acid derivatives: methyl 5-(2',4'-dichlorophenoxy)-2-nitrobenzoate ("bifenox"), 5-(2'-chloro-4'-trifluoromethylphenoxy)-2-nitrobenzoic acid ("acifluorfen") and 2,6-dichlorobenzonitrile ("dichlobenil");

nitroanilines: 2,6-dinitro-N,N-dipropyl-4-trifluoromethylaniline ("trifluralin") and N-(1'-ethylpropyl)-2,6-dinitro-3,4-xylidine ("pendimethaline");

oxadiazolones: 5-tert.-butyl-3-(2',4'-dichloro-5'-isopropoxyphenyl)-1,3,4-oxadiazol-2-one ("oxadiazon");

phosphates: S-2-methylpiperidino-carbonylmethyl 0,0-dipropyl phosphorodithioate ("piperophos");

pyrazoles: 1,3-dimethyl-4-(2',4'-dichlorobenzoyl)-5-(4'-tolylsulfonyloxy)-pyrazole; and 2-[1-(ethoxyimino)-butyl]-5-[2-(ethylthio)-propyl]-3-allyloxyamino)-butylidene]-5,5-dimethyl-4-methoxycarbonylcyclohexane-1,3-dione.

The compounds of the formula I are particularly suitable for protecting cultivated plants from the harmful effects of herbicides of the formula A

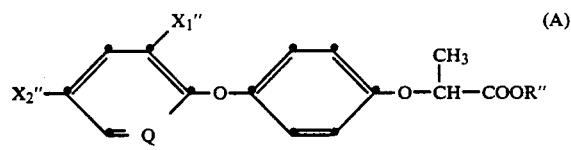

in which X''₁ is hydrogen or halogen, X''₂ is hydrogen, halogen or trifluoromethyl, Q is the fragment =N— or =CH—, R'' is $C_1$–$C_4$-alkyl, which is unsubstituted or substituted by $C_1$–$C_{14}$-alkoxy, or is $C_3$–$C_4$-alkenyl, $C_3$–$C_4$-alkinyl or

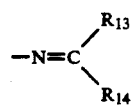

and $R_{13}$ is $C_1$–$C_4$-alkyl and $R_{14}$ is $C_1$–$C_4$-alkyl, or $R_{13}$ and $R_{14}$ together are $C_1$–$C_5$-alkylene.

Cultivated plants which are particularly suitable for being protected from agrochemicals by quinoline derivatives of the formula I are those which are important in the foodstuffs or textile sector, for example cultivated millet, rice, maize, species of cereal (wheat, rye, barley, oats), cotton, sugar beet, sugar cane and soybean.

The protective action of compounds of the formula I on cereals against the harmful effects of herbicides such as diphenyl ethers and substituted pyridyloxyphenoxypropionic acid esters, especially 2-propinyl 2-[4-(3,5-dichloropyridyl-2-oxy)-phenoxy]-propionate, is particularly worth mentioning.

A suitable method for protecting cultivated plants using compounds of the formula I comprises treating cultivated plants, parts of these plants or soil intended for growing the cultivated plants with a compound of the formula I or a composition containing such a compound, before or after the vegetable material is introduced into the soil. The treatment can be carried out before, at the same time as or after the use of the agrochemicals. Parts of plants are, in particular, those which are capable of reproduction of a plant, for example seeds, fruit, parts of the stem and branches (cuttings), as well as roots, tubers and rhizomes.

The present invention also relates to a method of selectively combating weeds in crops of cultivated plants in which the crops of cultivated plants, parts of the cultivated plants or areas for growing cultivated plants are treated with a herbicide and a compound of the formula I, or a composition containing this combination. The present invention also relates to compositions containing the herbicide/antidote combination.

The weeds to be combated can be either monocotyledonous or dicotyledonous weeds.

The cultivated plants or parts of these plants are, for example, those listed above. Areas for growing are the areas of soil on which cultivated plants are already growing or areas of soil which have been sown, as well as soils intended for growing cultivated plants.

The amount of antidote to be applied in relation to the agrochemical largely depends on the method of use. In the treatment of fields, which is carried out either using tank mixing or by separate application of the agrochemical and the antidote, the ratio of antidote to agrochemical is as a rule 1:100 to 10:1, preferably 1:5 to 8:1 and especially 1:1.

In contrast, in seed dressing and similar methods of use, far smaller amounts of antidote are required in relation to the amount of agrochemical applied per ha of area for growing. In the case of seed dressing, 0.1 to 10 g of antidote/kg of seed, preferably 1 to 2 g, are as a rule applied. If the antidote is applied shortly before sowing with swelling of the seed, antidote solutions containing the active substance in a concentration of 1 to 10,000 ppm, preferably 100 to 1,000 ppm, are advantageously used.

The compounds of the formula I can be used by themselves or together with inert adjuvants and/or the agrochemicals to be antagonised.

The present application thus also relates to compositions containing compounds of the formula I and inert adjuvants and/or agrochemicals to be antagonised, in particular plant protection agents and especially herbicides.

For application as an antidote or growth regulator, the compounds of the formula I or combinations of compounds of the formula I with agrochemicals to be antagonised are advantageously used together with the adjuncts conventionally used in the art of formulation, and are thus processed in a known manner to, for example, emulsion concentrates, brushable pastes, solutions which can be directly sprayed or diluted, dilute emulsions, wettable powders, soluble powders, dusts, granules and encapsulations in, for example, polymeric substances. The methods of use, such as spraying, misting, dusting, scattering, brushing or watering, are chosen according to the intended aims and the given conditions, in the same way as the type of composition.

The formulations, i.e. the compositions containing the active substance of the formula I or a combination of active substance of the formula I and agrochemical to be antagonised, with or without a solid or liquid adjuvant, preparations or combinations are prepared in a known manner, for example by intimate mixing and/or grinding of the active substances with extenders, for example with solvents, solid carriers and, if appropriate, surface-active compounds (surfactants).

Solvents include: aromatic hydrocarbons, preferably $C_8$ to $C_{12}$ fractions, for example xylene mixtures or substituted naphthalenes, phthalic acid esters, such as dibutyl phthalate or dioctyl phthalate, aliphatic hydrocarbons, such as cyclohexane or paraffins, alcohols and glycols and ethers and esters thereof, such as ethanol, ethylene glycol and ethylene glycol monomethyl or monoethyl ether, ketones, such as cyclohexanone, strongly polar solvents, such as N-methyl-2-pyrrolidone, dimethylsulfoxide and dimethylformamide, and vegetable oils, which may be epoxidised, such as epoxidised coconut oil or soybean oil; and water.

Ground natural rocks, such as calcite, talc, kaolin, montmorillonite or attapulgite, are as a rule used as solid carriers, for example for dusts and dispersible powders. Highly disperse silicic acid or highly disperse absorbent polymers may also be added to improve the physical properties. Suitable granular, adsorptive carriers for granules are porous types, for example pumice, crushed brick, sepiolite or bentonite, and examples of suitable non-sorptive carriers are calcite and sand. A large number of pregranulated materials of inorganic or organic nature can also be used, such as, in particular, dolomite or comminuted plant residues.

The surface-active compounds depend on the type of active substance of the formula I to be formulated and, where relevant, also of the agrochemical to be antagonised, and are non-ionic, cationic and/or anionic surfactants with good emulsifying, dispersing and wetting properties. Surfactants are also to be understood as meaning mixtures of surfactants.

Suitable anionic surfactants can be either so-called water-soluble soaps or water-soluble synthetic surface-active compounds.

Suitable soaps are alkali metal, alkaline earth metal or substituted or unsubstituted ammonium salts of higher fatty acids ($C_{10}$--$C_{22}$, for example the Na or K salts of oleic acid or stearic acid, or of natural fatty acid mixtures, which can be isolated from, for example, coconut oil or tallow oil. The fatty acid methyl-laurin salts are also suitable.

However, so-called synthetic surfactants are more frequently used, especially fatty sulfonates, fatty sulfates, sulfonated benzimidazole derivatives or alkylarylsulfonates.

The fatty sulfonates or sulfates are as a rule in the form of alkali metal, alkaline earth metal or substituted or unsubstituted ammonium salts and contain an alkyl radical having 8 to 22C atoms, alkyl also including the alkyl moiety of acyl radicals, for example the Na or Ca salt of lignin-sulfonic acid, of dodecylsulfuric acid ester or of a fatty alcohol sulfate mixture prepared from natural fatty acids. These also include the salts of sulfuric acid esters and sulfonic acids of fatty alcohol/ethylene oxide adducts. The sulfonated benzimidazole derivatives preferably contain 2 sulfonic acid groups and a fatty acid radical having 8 to 22C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensate.

Corresponding phosphates, for example salts of the phosphoric acid ester of a p-nonylphenol-(4–14)-ethylene oxide adduct or phospholipids are also suitable.

Particularly suitable non-ionic surfactants are polyglycol ether derivatives of aliphatic or cycloaliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble adducts, containing 20 to 250 ethylene glycol ether groups and 10 to 100 propylene glycol ether groups, of polyethylene oxide onto polypropylene glycol, ethylenediaminopolypropylene glycol and alkylpolypropylene glycol with 1 to 10 carbon atoms in the alkyl chain. The above compounds usually contain 1 to 5 ethylene glycol units per propylene glycol unit.

Examples of non-ionic surfactants are nonylphenolpolyethoxyethanols, castor oil polyglycol ethers, polypropylene-polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, can also be used.

The cationic surfactants are, in particular, quaternary ammonium salts which contain at least one alkyl radical having 8 to 22C atoms as a substituent on N, and lower non-halogenated or halogenated alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants conventionally used in the art of formulation are described in, inter alia, the following publications: "McCutcheon's Detergents and Emulsifiers Annual" MC Publishing Corp., Ringwood N.J. 1980, Sisely and Wood, "Encyclopedia of Surface Active Agents", Chemical Publishing Co., Inc. New York, 1980.

The agrochemical preparations as a rule contain 0.1 to 99%, in particular 0.1 to 95%, of active substance of the formula I, 99.9 to 1%, in particular 99.8 to 5%, of a solid or liquid adjuvant and 0 to 25%, in particular 0.1 to 25%, of a surfactant.

Whilst concentrated compositions are preferred as commercial goods, the final consumer as a rule uses dilute compositions.

The compositions can also contain other adjuvants, such as stabilisers, anti-foaming agents, viscosity regulators, binders, tackifiers and fertilisers or other active substances for achieving particular effects.

Compounds of the formula I or compositions containing them are used for protecting crop plants from the harmful effects of agrochemicals by various methods and techniques, for example as follows:

i) Seed dressing a) Dressing the seed with a wettable powder formulation of the active substance by shaking in a vessel until uniform distribution over the seed surface is achieved (dry dressing). About 10 to 500 g of active substance of the formula I (40 g to 2 kg of wettable powder) are thereby used per 100 kg of seed.

b) Dressing the seed with an emulsion concentrate of the active substance of the formula I by method a) (wet dressing).

c) Dressing by immersing the seed in a liquor containing 50–3,200 ppm of active substance of the formula I for 1 to 72 hours, and if necessary subsequently drying the seed (steeping).

Dressing of the seed or treatment of the germinated seedling are of course the preferred methods of application because treatment with the active substance is directed entirely towards the target crop. As a rule 10 g to 500 g, preferably 50 to 250 g, of active substance are used per 100 kg of seed, but deviation upwards or downwards from the given threshold concentrations is also possible (repeated dressing), depending on the method, which also permits addition of other active substances or micronutrients.

ii) Application from tank mixing

A liquid preparation of a mixture of antidote and herbicide (mixing proportions of between 10:1 and 1:10) is used, the amount of herbicide applied being 0.1 to 10 kg per hectare. Such a tank mixture is preferably applied before or immediately after sowing or is incorporated into the soil, which has not yet been sown, down to a depth of 5 to 10 cm.

iii) Application into the seed furrow

The antidote is introduced as an emulsion concentrate or wettable powder or as granules into the open sown seed furrows, and the herbicide is then applied by the pre-emergence method in the normal manner after the seed furrow has been covered.

iv) Controlled release of active substance

The active substance is applied to mineral carrier granules or polymerised granules (urea/formaldehyde) in solution and the granules are left to dry. If necessary, a coating which permits metered release of the active substance over a certain period of time can be applied (coated granules).

Compounds of the formula I are prepared by
a) reacting a compound of the formula II

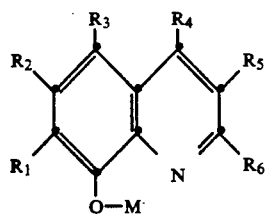
(II)

in which $R_1$, $R_2$, $R_3$, $R_4$, $R_5$ and $R_6$ are as defined for formula I and M is hydrogen or an alkali metal or alkaline earth metal atom, with a compound of the formula III

 (III)

in which X and Y are as defined for formula I and Z is a detachable radical, or b) for the preparation of compounds of the formula I in which Y is —$COOR_7$, reacting an acid halide of the formula IV

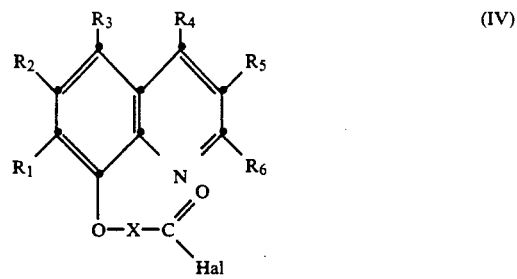 (IV)

in which $R_1$, $R_2$, $R_3$, $R_4$, $R_5$, $R_6$ and X are as defined for formula I and Hal is a halogen atom, with a compound of the formula V

 (V)

in which $R_7$ is as defined for formula I and M' is hydrogen or an alkali metal or alkaline earth metal atom, or c) for the preparation of compounds of the formula I in which Y is —$COSR_8$, reacting an acid halide of the formula VI

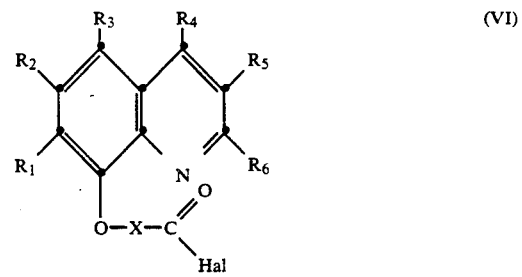 (VI)

in which $R_1$, $R_2$, $R_3$, $R_4$, $R_5$, $R_6$ and X are as defined for formula I and Hal is a halogen atom, with a compound of the formula VII

 (VII)

in which $R_8$ is as defined for formula I and M'' is hydrogen or an alkali metal or alkaline earth metal atom, or d) for the preparation of compounds of the formula I in which Y is —$CONR_9R_{10}$, reacting an acid halide of the formula VIII

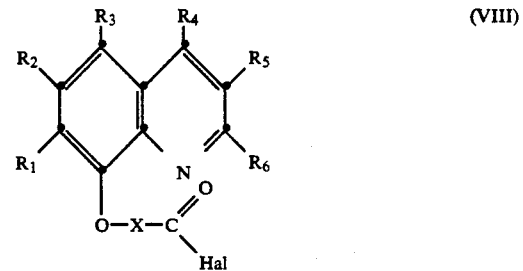 (VIII)

in which $R_1$, $R_2$, $R_3$, $R_4$, $R_5$, $R_6$ and X are as defined for formula I and Hal is a halogen atom, with a compound of the formula IX

 (IX)

in which $R_9$ and $R_{10}$ are as defined for formula I, or e) for the preparation of compounds of the formula I in which Y is $COOR_7$, reacting a compound of the formula X

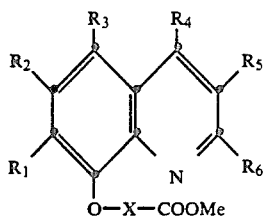

in which $R_1, R_2, R_3, R_4, R_5, R_6$ and X are as defined for formula I and Me is an alkali metal, alkaline earth metal, lead or silver atom, with a compound of the formula XI Hal—$R_7$ (XI)

in which $R_7$ is as defined for formula I and Hal is a halogen atom, or f) for the preparation of compounds of the formula I in which Y is $-COSR_8$, reacting a compound of the formula XII

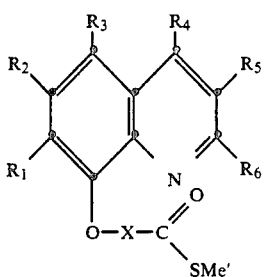

in which $R_1, R_2, R_3, R_4, R_5, R_6$ and X are as defined for formula I and Me' is an alkali metal, alkaline earth metal, lead or silver atom, with a compound of the formula XIII Hal—$R_8$ (XIII)

in which $R_8$ is as defined for formula I and Hal is a halogen atom, or g) for the preparation of compounds of the formula I in which Y is $-COOR_7$, reacting a compound of the formula XIV

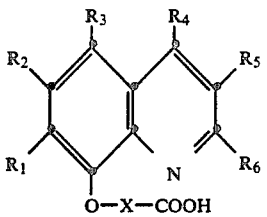

in which $R_1, R_2, R_3, R_4, R_5, R_6$ and X are as defined for formula I, with a compound of the formula XV

HO—$R_7$ (XV)

in which $R_7$ is as defined for formula I or h) for the preparation of compounds of the formula I in which Y is $-COSR_8$, reacting a compound of the formula XVI

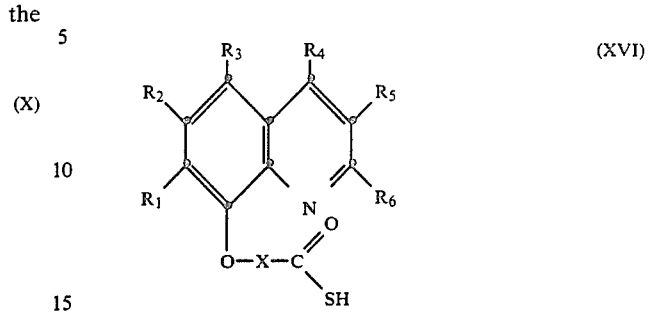

in which $R_1, R_2, R_3, R_4, R_5, R_6$ and X are as defined for formula I, with a compound of the formula XVII

HO—$R_8$ (XVII)

in which $R_8$ is as defined for formula I, or i) for the preparation of compounds of the formula I in which Y is $-COOR_7$, reacting a compound of the formula Ia

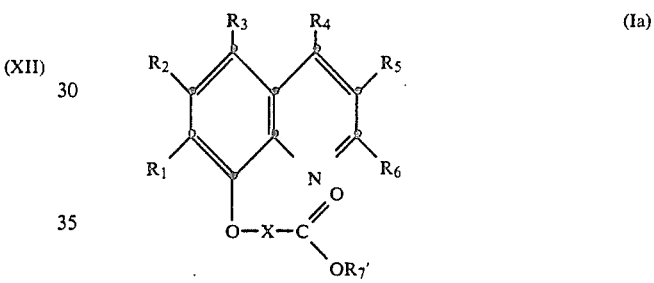

in which $R_1, R_2, R_3, R_4, R_5, R_6$ are as defined for formula I and $R_7'$ is as defined for $R_7$ in formula I, with a compound of the formula XVIII

HO—$R_7''$ (XVIII)

in which $R_7''$ is as defined for $R_7$ in formula I but is not identical to $R_7'$, or k) for the preparation of compounds of the formula I in which Y is $-COSR_8$, reacting a compound of the formula Ib

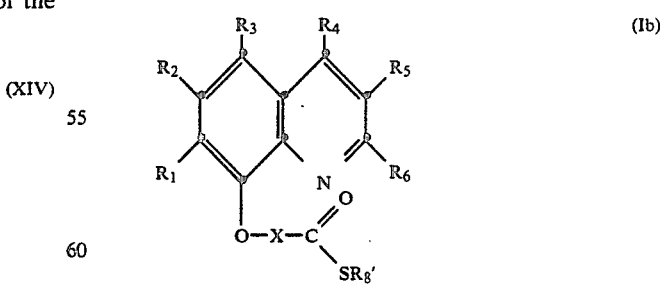

which $R_1, R_2, R_3, R_4, R_5, R_6$ and X are as defined for formula I and $R_8'$ is as defined for $R_8$ in formula I, with a compound of the formula XIX $HSR_8''$ (XIX)

in which R$_8$ is as defined for R$_8$ in formula I but is not identical to R$_8$, or l) for the preparation of compounds of the formula I in which Y is —CONR$_9$R$_{10}$, reacting a compound of the formula XX

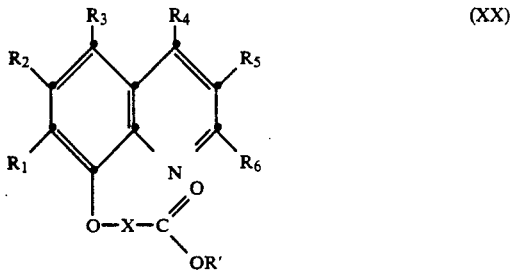

in which R$_1$, R$_2$, R$_3$, R$_4$, R$_5$, R$_6$ and X are as defined for formula I and R' is an aliphatic, acyclic hydrocarbon radical, with a compound of the formula XXI

in which R$_9$ and R$_{10}$ are as defined for formula I, or m) for the preparation of compounds of the formula I in which X is —CH$_2$CH$_2$—, reacting a compound of the formula XXII

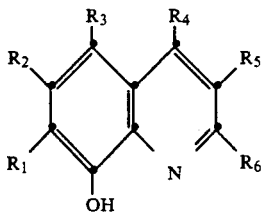

in which R$_1$, R$_2$, R$_3$, R$_4$, R$_5$ and R$_6$ are as defined for formula I, with a compound of the formula XXIII

in which Y is as defined for formula I, or n) for the preparation of compounds of the formula I in which Y is a substituted or unsubstituted oxazolin-2-yl radical, cyclising a compound of the formula XXIV

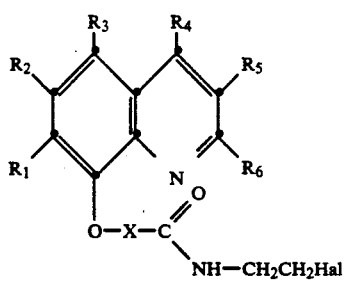

in which R$_1$, R$_2$, R$_3$, R$_4$, R$_5$, R$_6$ and X are as defined for formula I and Hal is a halogen atom, in particular a chlorine or bromine atom, in the presence of an acid-binding agent.

A detachable radical Z in the compound of the formula III in process variant a) is, in particular, a halogen atom or a methylsulfonyloxy, phenylsulfonyloxy or p-tolylsulfonyloxy group. Halogen is fluorine, chlorine, bromine or iodine, preferably chlorine or bromine.

If M is hydrogen in the compound of the formula II and Z is a halogen atom in the compound of the formula III, the reaction can preferably be carried out in the presence of a conventional proton acceptor. Moreover, if Z is a halogen atom in the compound of the formula III, addition of a small amount of alkali metal iodide has a catalytic effect.

In process variants b), c) and d), Hal in the compounds of the formulae IV, VI and VIII is a halogen atom, such as fluorine, chlorine, bromine or iodine, preferably chlorine or bromine.

If M' or M" is hydrogen in the compounds of the formulae V or VII in process variants b) and c), the reaction is preferably carried out, as in the case of process variant d), in the presence of an acid-binding agent.

Acid halides of the compounds IV, VI and VII are preferably hydrohalic acids, in particular hydrochloric or hydrobromic acid.

In process variants g) and h), the water formed in the reaction can be removed from the reaction mixture by means of, for example, a water separator. A catalytic effect is achieved by addition of acid.

The trans-esterification in process variants i) and k) can be influenced catalytically by addition of acid or base. The reaction is advantageously carried out with an excess of compounds of the formula XVIII or XIX.

In process variant l), R' in the compounds of the formula XX is preferably an alkyl radical having 1 to 6 carbon atoms, in particular methyl or ethyl.

The reactions in process variants a) to n) are advantageously carried out in the presence of solvents which are inert towards the reactants. Examples of suitable inert solvents are hydrocarbons, such as benzene, toluene, xylene, petroleum ether or cyclohexane, ethers, for example diethyl ether, tetrahydrofuran, dioxane, dimethoxyethane or diethylene glycol dimethyl ether, acid amides, for example dimethylformamide, 2-pyrrolidinone or hexamethylphosphoric acid triamide, and sulfoxides, for example dimethylsulfoxide.

Examples of acid-binding agents which can be used are alkali metal and alkaline earth metal hydroxides or alcoholates, alkali metal carbonates and tertiary organic bases.

The reaction temperatures are in general within a range from 0° to 200° C., in particular in the range from 50° to 150° C.

The starting substances used in process variants a) to n) are known, or they can be prepared analogously to known processes.

A number of quinoline derivatives and their use in various fields of application are known from the literature. Thus, for example, U.S. Pat. No. 4,176,185, British Patent Specifications 760,319, 989,578, 1,003,477 and 1,003,478, Swiss Patent Specification 408,007, German Offenlegungsschrift 2,546,845, Areschka, A. et al., Eur. J. Med.Chem.-Chimica Therapeutica, Sept.-Oct. 1975-10, No.5, 463–469, Major R. T. et al., J. Med. Pharm. Chem. 4, 317–326, 1961, and Thompson, H. E., Botan. Gaz. 107, 476–507, 1946, describe the use of quinoline derivatives in the therapeutic field, as a starting substance for the preparation of therapeutic active ingredients, as agents for promoting growth in animals, as plant growth inhibitors or as herbicides.

The present invention relates to novel quinoline derivatives of the formula I. Novel compounds of the formula I which belong to one of the above sub-groups o), p), q), r), s), t), u), v), w), x), y), z), z¹), z²), z³ and z⁴) are particularly worth mentioning.

EXAMPLE 1

23.2 g of 8-hydroxyquinoline are dissolved in 400 ml of butan-2-one, under the influence of heat, and 30 g of potassium carbonate are added in portions. The mixture is refluxed for one hour. 2 g of potassium iodide are then added dropwise, followed by 40 g of methyl 2-bromopropionate in 100 ml of butan-2-one in the course of one hour, with stirring and boiling. The mixture is then refluxed for another 10 hours. After cooling to room temperature, the mixture is poured onto 1 liter of water and extracted with three 200 ml portions of ethyl acetate. The combined extracts are washed once with 50 ml of water, dried over sodium sulfate and filtered. The solvent is evaporated off and the oily residue is crystallised by trituration with petroleum ether. After recrystallisation from hexane, methyl 2-(8-quinolinoxy)-propionate (compound No.3) is obtained in the form of beige-coloured crystals of melting point 70° to 72° C.

The following compounds of the formula I listed in Table 1, together with the compound of the above example, can also be prepared by a method similar to one of the methods described above:

TABLE 1

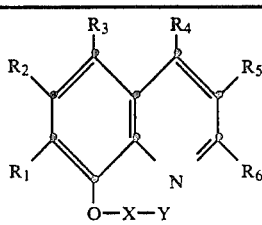

| Compound No. | $R_1$ | $R_2$ | $R_3$ | $R_4$ | $R_5$ | $R_6$ | X | Y | Physical constants |
|---|---|---|---|---|---|---|---|---|---|
| 1 | Cl | H | Cl | H | H | H | —CH(CH₃)— | —COOCH₃ | Melting point 65–66° C. |
| 2 | H | H | H | H | H | H | —CH(CH₃)— | —COO(CH₂)₁₃—CH₃ | |
| 3 | H | H | H | H | H | H | —CH(CH₃)— | —COOCH₃ | Melting point 70–72° C. |
| 4 | H | H | H | H | H | H | —CH₂— | —COOH·H₂O | Melting point 184–185° C. |
| 5 | H | H | H | H | H | H | —CH(CH₃)— | —COOH | |
| 6 | H | H | H | H | H | H | —CH₂— | —COOCH₂CH₂OCH₃ | Melting point 80–82° C. |
| 7 | H | H | H | H | H | H | —CH(CH₃)— | —COOCH₂CH₂OCH₃ | |
| 8 | H | H | H | H | H | H | —CH₂— | —COOCH₃ | Melting point 46.5–67.0° C. |
| 9 | H | H | H | H | H | H | —CH(CH₃)— | —COOCH₂CH₂OC₂H₅ | |
| 10 | H | H | H | H | H | H | —CH(CH₃)— | —COOCH(CH₂CH(CH₃)CH₃)(CH₂—C(=CH₂)—CH=CH₂) | |
| 11 | H | H | H | H | H | H | —CH₂— | —COOC₂H₅·H₂O | Melting point 56–59° C. |
| 12 | H | H | H | H | H | H | —CH(CH₃)— | —COOCH₂CH(CH₃)₂ | |

TABLE 1-continued

| | | | | | | | | | |
|---|---|---|---|---|---|---|---|---|---|
| 13 | H | H | H | H | H | H | —CH(CH$_3$)— | —CONH(CH$_2$)$_3$OC$_2$H$_5$ | Melting point 54–56° C. |
| 14 | H | H | H | H | H | H | —CH(CH$_3$)— | —COOCH$_2$-(oxiranyl) | |
| 15 | H | H | H | H | H | H | —CH(CH$_3$)— | —COOC$_2$H$_5$ | |
| 16 | H | H | H | H | H | H | —CH(CH$_3$)— | —CONHCH$_2$CH(CH$_3$)$_2$ | |
| 17 | H | H | H | H | H | H | —CH(CH$_3$)— | —CONHC$_2$H$_5$ | Melting point 86–88° C. |
| 18 | H | H | H | H | H | H | —CH(CH$_3$)— | —COOCH$_2$CH$_2$CH(CH$_3$)$_2$ | |
| 19 | H | H | H | H | H | H | —CH(CH$_3$)— | —CON(C$_2$H$_5$)(C$_6$H$_5$) | |
| 20 | H | H | H | H | H | H | —CH$_2$— | —COOC$_3$H$_7$n | Melting point 28–31° C. |
| 21 | H | H | H | H | H | H | —CH(CH$_3$)— | —COOCH(CH$_3$)$_2$ | |
| 22 | H | H | H | H | H | H | —CH(CH$_3$)— | —CONH-(2-C$_2$H$_5$-C$_6$H$_4$) | |
| 23 | H | H | H | H | H | H | —CH(CH$_3$)— | —CONH—CH$_2$-(oxiranyl) | |
| 24 | H | H | H | H | H | H | —CH(CH$_3$)— | —CON(C$_2$H$_5$)(CH$_2$C$_6$H$_5$) | |
| 25 | H | H | H | H | H | H | —CH(CH$_3$)— | —CONH—CH(CH$_3$)$_2$ | |
| 26 | H | H | H | H | H | H | —CH(CH$_3$)— | —COOCH$_2$CH(C$_2$H$_5$)$_2$ | |
| 27 | H | H | H | H | H | H | —CH(CH$_3$)— | —CON(C$_2$H$_5$)(C$_4$H$_9$n) | |

TABLE 1-continued

| No. | | | | | | | Linker | Substituent | Notes |
|---|---|---|---|---|---|---|---|---|---|
| 28 | H | H | H | H | H | H | —CH$_2$— | —COOC$_3$H$_7$iso | n$_D^{23}$ = 1.5696 |
| 29 | H | H | H | H | H | H | —CH(CH$_3$)— | —COOCH$_2$CH$_2$OH | |
| 30 | H | H | H | H | H | H | —CH(CH$_3$)— | —COSCH(CH$_3$)$_2$ | |
| 31 | H | H | H | H | H | H | —CH(CH$_3$)— | —CONHCH$_2$CH(C$_2$H$_5$)(CH$_2$)$_3$CH$_3$ | |
| 32 | H | H | H | H | H | H | —CH$_2$— | —CONHCH$_3$·H$_2$O | Melting point 74–81° C. |
| 33 | H | H | H | H | H | H | —CH(CH$_3$)— | —COSC$_2$H$_5$ | |
| 34 | H | H | H | H | H | H | —CH(CH$_3$)— | —COOCH$_2$CH$_2$OCH(CH$_3$)$_2$ | |
| 35 | H | H | H | H | H | H | —CH(CH$_3$)— | —COO—C$_6$H$_4$—C$_2$H$_5$ | |
| 36 | H | H | H | H | H | H | —CH$_2$— | —CON(CH$_3$)$_2$ | Melting point 142–145° C. |
| 37 | H | H | H | H | H | H | —CH$_2$— | —CONHC$_2$H$_5$ | n$_D^{22.5}$ = 1.6002 |
| 38 | H | H | H | H | H | H | —CH(CH$_3$)— | —COOCH$_2$CH=CH$_2$ | |
| 39 | H | H | NO$_2$ | H | H | H | —CH(CH$_3$)— | —COOH | |
| 40 | H | H | H | H | H | H | —CH(CH$_3$)— | —CONHCH$_2$—CH=CH$_2$ | |
| 41 | H | H | H | H | H | H | —CH(CH$_3$)— | —COO—C$_6$H$_4$—CH$_3$ | |
| 42 | H | H | H | H | H | H | —CH(CH$_3$)— | —CONHCH$_2$CH$_2$Br | |
| 43 | H | H | H | H | H | H | —CH(CH$_3$)— | —CONHCH$_2$CH$_2$—N(morpholino)O | |
| 44 | H | H | H | H | H | H | —CH(CH$_3$)— | —COOCH$_2$—C(CH$_3$)=CH$_2$ | |

TABLE 1-continued

| | | | | | | | | | |
|---|---|---|---|---|---|---|---|---|---|
| 45 | H | H | H | H | H | H | —CH(CH₃)— | —CONH—C₆H₄(o-CN) | |
| 46 | H | H | H | H | H | H | —CH₂— | —CON(C₂H₅)₂ | |
| 47 | H | H | H | H | H | H | —CH(CH₃)— | —CONH—C₆H₄(o-CF₃) | |
| 48 | H | H | NO₂ | H | H | H | —CH(CH₃)— | —COOCH₂CH₂OCH₃ | |
| 49 | H | H | H | H | H | H | —CH(CH₃)— | —CONHCH(C₂H₅)CH₂OH | |
| 50 | H | H | H | H | H | H | —CH(CH₃)— | —COOCH₂CH₂OCH₃ | |
| 51 | H | H | H | H | H | H | —CH(CH₃)— | —CONH—C(C₂H₅)₂—CH₂OH | |
| 52 | H | H | H | H | H | H | —CH₂— | —CONH₂ | |
| 53 | H | H | H | H | H | H | —CH(CH₃)— | —CONH—(6-methylpyridin-2-yl) | |
| 54 | H | H | H | H | H | H | —CH(CH₃)— | —CONH—C₆H₃(2-CH₃, 4-NO₂) | |
| 55 | H | H | H | H | H | H | —CH(CH₃)— | —CONHCH₂CH₂OCH₃ | |
| 56 | H | H | H | H | H | H | —CH(CH₃)— | —CONH(CH₂)₃OH | Melting point 120–122° C. |
| 57 | H | H | H | H | H | H | —CH(CH₃)— | —CONH—(thiazol-2-yl) | |
| 58 | H | H | H | H | H | H | —CH₂— | —COOCH₂CH₂OC₂H₅ | $n_D^{24} = 1.5673$ |
| 59 | H | H | H | H | H | H | —CH(CH₃)— | —CONH₂ | |

TABLE 1-continued

| | | | | | | | | | |
|---|---|---|---|---|---|---|---|---|---|
| 60 | H | H | H | H | H | H | —CH(CH₃)— | —COOCH₂—C₆H₄—OCH₃ | |
| 61 | H | H | H | H | H | H | —CH(CH₃)— | —CONH—C₆H₅ | |
| 62 | H | H | NO₂ | H | H | H | —CH(CH₃)— | —COOCH₃ | |
| 63 | H | H | H | H | H | H | —CH(CH₃)— | —CONH—C₆H₄(OCH₃) | |
| 64 | H | H | H | H | H | H | —CH(CH₃)— | —CONH(CH₂)₃OCH₃ | |
| 65 | H | H | H | H | H | H | —CH(CH₃)— | —CONHCH₂—C₆H₅ | Melting point 88–90° C. |
| 66 | H | H | NO₂ | H | H | H | —CH(CH₃)— | —COOC₂H₅ | |
| 67 | H | H | H | H | H | H | —CH(CH₃)— | —CONHCH₃ | |
| 68 | H | H | H | H | H | H | —CH(CH₃)— | —CON(CH₂CH₂OH)(CH₂—C₆H₅) | |
| 69 | H | H | H | H | H | H | —CH₂— | —CONH(CH₂)₃CH₃ | Melting point 66–68° C. |
| 70 | H | H | H | H | H | H | —CH(CH₃)— | —CON(CH(CH₃)₂)(CH₂—C₆H₅) | |
| 71 | H | H | H | H | H | H | —CH(CH₃)— | —CON(CH₃)(CH₂CH₂OH) | $n_D^{22} = 1.6054$ |
| 72 | H | H | H | H | H | H | —CH(CH₃)— | —CON(CH₃)(CH₂—C₆H₅) | |
| 73 | H | H | NO₂ | H | H | H | —CH(CH₃)— | —COOC₃H₇n | |

TABLE 1-continued

| # | | | | | | | | | |
|---|---|---|---|---|---|---|---|---|---|
| 74 | H | H | H | H | H | H | $-\underset{\underset{CH_3}{\mid}}{CH}-$ | $-CONH(CH_2)_3-N\underset{CH_2CH_2OH}{\overset{CH_2CH_2OH}{\diagdown}}$ | |
| 75 | H | H | $NO_2$ | H | H | H | $-\underset{\underset{CH_3}{\mid}}{CH}-$ | $-COOC_3H_7\text{iso}$ | |
| 76 | H | H | H | H | H | H | $-\underset{\underset{CH_3}{\mid}}{CH}-$ | $-CON(CH_2\overset{OH}{\overset{\mid}{C}H}CH_3)_2$ | |
| 77 | H | H | H | H | H | H | $-\underset{\underset{CH_3}{\mid}}{CH}-$ | $-CON(CH_2CH_2OCH_3)_2$ | |
| 78 | H | H | H | H | H | H | $-\underset{\underset{CH_3}{\mid}}{CH}-$ | $-CONH(CH_2)_3NHCH_3$ | |
| 79 | H | H | H | H | H | H | $-\underset{\underset{CH_3}{\mid}}{CH}-$ | $-COOCH_2CH_2Br$ | |
| 80 | H | H | $NO_2$ | H | H | H | $-\underset{\underset{CH_3}{\mid}}{CH}-$ | $-CONHCH_3$ | |
| 81 | H | H | H | H | H | H | $-\underset{\underset{CH_3}{\mid}}{CH}-$ | $-COO(CH_2)_4OH$ | |
| 82 | H | H | H | H | H | H | $-CH_2-$ | $-CON\underset{CH_2CH_2OH}{\overset{CH_3}{\diagdown}}$ | Melting point 146–149° C. |
| 83 | H | H | H | H | H | H | $-\underset{\underset{CH_3}{\mid}}{CH}-$ | $-COOCH\underset{\underset{CH_3}{\mid}}{\overset{CH_3}{\diagup}}\\ \quad CH-OH$ | |
| 84 | H | H | H | H | H | H | $-\underset{\underset{CH_3}{\mid}}{CH}-$ | $-COOCH_2\overset{\overset{CH_3}{\mid}}{C}HCH_2CH_3$ | |
| 85 | H | H | H | H | H | H | $-\underset{\underset{CH_3}{\mid}}{CH}-$ | $-COOCH_2-C\equiv C-CH_2OH$ | |
| 86 | H | H | H | H | H | H | $-CH_2-$ | $-COOCH_2-\underset{O}{\triangle}$ | Viscous mass |
| 87 | H | H | H | H | H | H | $-\underset{\underset{CH_3}{\mid}}{CH}-$ | $-COOC_4H_9 n$ | |
| 88 | H | H | H | H | H | H | $-\underset{\underset{CH_3}{\mid}}{CH}-$ | $-COO-\overset{\overset{CH_3}{\mid}}{\underset{\underset{CH_3}{\mid}}{C}}-CH_2CH_3$ | |
| 89 | H | H | H | H | H | H | $-\underset{\underset{CH_3}{\mid}}{CH}-$ | $-COO\overset{\overset{CH_3}{\mid}}{C}H-C_2H_5$ | |
| 90 | H | H | $NO_2$ | H | H | H | $-\underset{\underset{CH_3}{\mid}}{CH}-$ | $-CON\underset{CH_3}{\overset{CH_3}{\diagdown}}$ | |

TABLE 1-continued

| | | | | | | | | | |
|---|---|---|---|---|---|---|---|---|---|
| 91 | H | H | H | H | H | H | $-\underset{\underset{CH_3}{|}}{CH}-$ | $-CONH(CH_2)_3CH_3 \cdot H_2O$ | Melting point 73–76° C. |
| 92 | H | H | H | H | H | H | $-\underset{\underset{CH_3}{|}}{CH}-$ | $-COO-\underset{\underset{CH_3}{|}}{\overset{CH_3}{}}CH-COOC_4H_9n$ | |
| 93 | H | H | H | H | H | H | $-\underset{\underset{CH_3}{|}}{CH}-$ | $-CONH-\underset{\underset{CH_3}{|}}{\overset{CH_3}{}}CH-C_2H_5$ | |
| 94 | H | H | $NO_2$ | H | H | H | $-\underset{\underset{CH_3}{|}}{CH}-$ | $-CONH_2$ | |
| 95 | H | H | H | H | H | H | $-\underset{\underset{CH_3}{|}}{CH}-$ | $-CON\underset{(CH_2)_3CH_3}{\overset{CH_2CH_2OH}{\diagup}}$ | |
| 96 | H | H | $NO_2$ | H | H | H | $-\underset{\underset{CH_3}{|}}{CH}-$ | $-COOCH_2CH_2OC_2H_5$ | |
| 97 | H | H | H | H | H | H | $-\underset{\underset{CH_3}{|}}{CH}-$ | $-COS(CH_2)_3CH_3$ | |
| 98 | H | H | H | H | H | H | $-\underset{\underset{CH_3}{|}}{CH}-$ | $-COO-\text{(2-methylcyclohexyl)}$ | |
| 99 | H | H | H | H | H | H | $-\underset{\underset{CH_3}{|}}{CH}-$ | $-CON\underset{(CH_2)_3CH_3}{\overset{CH_3}{\diagup}}$ | |
| 100 | Br | H | Cl | H | H | H | $-CH_2-$ | $-COOCH_3$ | Melting point 126–128° C. |
| 101 | H | H | H | H | H | H | $-\underset{\underset{CH_3}{|}}{CH}-$ | $-COOCH_2CH_2OC_4H_9n$ | |
| 102 | Br | H | Cl | H | H | H | $-CH_2-$ | $-COOC_2H_5$ | |
| 103 | H | H | H | H | H | H | $-\underset{\underset{CH_3}{|}}{CH}-$ | $-COOCH_2CH_2Cl$ | |
| 104 | H | H | H | H | H | H | $-\underset{\underset{CH_3}{|}}{CH}-$ | $-CON(CH_3)\text{-cyclohexyl}$ | |
| 105 | H | H | H | H | H | H | $-\underset{\underset{CH_3}{|}}{CH}-$ | $-CONH-\text{C}_6\text{H}_4-Cl$ | |
| 106 | Br | H | Cl | H | H | H | $-CH_2-$ | $-COOC_3H_7n$ | |
| 107 | H | H | H | H | H | H | $-\underset{\underset{CH_3}{|}}{CH}-$ | $-COOCH_2-\text{C}_6\text{H}_4-Cl$ | |
| 108 | Br | H | Cl | H | H | H | $-CH_2-$ | $-CONHCH_3$ | |

TABLE 1-continued

| 109 | H | H | H | H | H | H | —CH(CH₃)— | —CONH—CH₂—C₆H₄—Cl |
| 110 | H | H | H | H | H | H | —CH(CH₃)— | —CON< (N-methylimidazoline) |
| 111 | H | H | H | H | H | H | —CH(CH₃)— | —COO—C₆H₃(CH₃)—Cl |
| 112 | H | H | H | H | H | H | —CH(CH₃)— | —COOCH₂CH(CH₃)CH₂CH₃ |
| 113 | H | H | H | H | H | H | —CH(CH₃)— | —COO—C₆H₄—Cl |
| 114 | H | H | H | H | H | H | —CH(CH₃)— | —COO(CH₂)₃Cl |
| 115 | H | H | H | H | H | H | —CH(CH₃)— | —CONH(CH₂)₃Cl |
| 116 | H | H | H | H | H | H | —CH(CH₃)— | —COOCH₂—CH(NO₂)—CH₃ |
| 117 | H | H | H | H | H | H | —CH(CH₃)— | —COS—C₆H₄—Cl |
| 118 | Br | H | Cl | H | H | H | —CH₂— | —CON(CH₃)₂ |
| 119 | H | H | H | H | H | H | —CH(CH₃)— | —COOCH₂—CH=CH—CH₃ |
| 120 | H | H | H | H | H | H | —CH(CH₃)— | —COO—C₆H₁₁ |
| 121 | H | H | H | H | H | H | —CH(CH₃)— | —CONH—C₆H₁₁ |
| 122 | H | H | H | H | H | H | —CH(CH₃)— | —CON(CH₃)(C₆H₁₁) |

TABLE 1-continued

| | | | | | | | | | |
|---|---|---|---|---|---|---|---|---|---|
| 123 | H | H | H | H | H | H | −CH(CH$_3$)− | −COO(CH$_2$)$_{10}$OH | |
| 124 | H | H | H | H | H | H | −CH(CH$_3$)− | −COO(CH$_2$)$_9$CH$_3$ | |
| 125 | H | H | H | H | H | H | −CH(CH$_3$)− | −CONH(CH$_2$)$_9$CH$_3$ | |
| 126 | H | H | H | H | H | H | −CH(CH$_3$)− | −CON(CH$_2$CH$_2$OH)$_2$ | |
| 127 | H | H | H | H | H | H | −CH(CH$_3$)− | −CON(C$_2$H$_5$)$_2$ | |
| 128 | Br | H | Cl | H | H | H | −CH$_2$− | −CONH$_2$ | |
| 129 | H | H | H | H | H | H | −CH(CH$_3$)− | −COOCH$_2$CH$_2$N(C$_2$H$_5$)$_2$ | |
| 130 | H | H | H | H | H | H | −CH(CH$_3$)− | −CONHCH$_2$CH$_2$N(C$_2$H$_5$)$_2$ | |
| 131 | H | H | H | H | H | H | −CH(CH$_3$)− | −COOCH$_2$CH$_2$OCH$_2$OC$_2$H$_5$ | |
| 132 | H | H | H | H | H | H | −CH(CH$_3$)− | −CON(morpholino) | Melting point 120–121° C. |
| 133 | H | H | H | H | H | H | −CH(CH$_3$)− | −CONH(CH$_2$)$_3$−N(C$_2$H$_5$)$_2$ | |
| 134 | H | H | H | H | H | H | −CH(CH$_3$)− | −COOCH$_2$CH$_2$OCH$_2$CH$_2$OC$_4$H$_9$n | |
| 135 | H | H | H | H | H | H | −CH(CH$_3$)− | −COOCH$_2$CH$_2$OCH$_2$CH$_2$OCH$_3$ | |
| 136 | H | H | H | H | H | H | −CH(CH$_3$)− | −COOCH$_2$CH$_2$OCH$_2$CH$_2$OH | |
| 137 | H | H | H | H | H | H | −CH(CH$_3$)− | −CON(CH$_2$CH=CH$_2$)$_2$ | |

-continued

| | | | | | | | | |
|---|---|---|---|---|---|---|---|---|
| 138 | H | H | H | H | H | H | −CH(CH₃)− | −CON(CH(CH₃)−)₂(H,O ring)  [morpholide-like: −CON with two CH(CH₃) groups bridged by H and O] |
| 139 | H | H | H | H | H | H | −CH(CH₃)− | −CONH(CH₂)₆NH₂ |
| 140 | H | H | H | H | H | H | −CH(CH₃)− | −COOCH₂CH(Br)−CH₂Br |
| 141 | H | H | H | H | H | H | −CH(CH₃)− | −CON(C₄H₉n)₂ |
| 142 | H | H | H | H | H | H | −CH(CH₃)− | −COO−(2-naphthyl) |
| 143 | H | H | H | H | H | H | −CH(CH₃)− | −CONH(CH₂)₈NH₂ |
| 144 | H | H | H | H | H | H | −CH(CH₃)− | −COOCH₂CH₂N(CH₂CH₂CH₂CH₃)₂ |
| 145 | H | H | H | H | H | H | −CH(CH₃)− | −CONHCH₂CH₂N(C₄H₉n)₂ |
| 146 | H | H | H | H | H | H | −CH(CH₃)− | −CONH(CH₂)₃NH₂ |
| 147 | H | H | H | H | H | H | −CH(CH₃)− | −COO−(2,4-di-tert-butylphenyl) |
| 148 | H | H | H | H | H | H | −CH(CH₃)− | −COO(CH₂)₁₇CH₃ |
| 149 | H | H | H | H | H | H | −CH(CH₃)− | −COOCH(CH₂Cl)₂ |
| 150 | H | H | H | H | H | H | −CH(CH₃)− | −CON(C₆H₁₁)₂ |
| 151 | H | H | H | H | H | H | −CH(CH₃)− | −CON(CH₂CH(CH₃)₂)₂ |
| 152 | H | H | H | H | H | H | −CH(CH₃)− | −COOCH₂CH₂NO₂ |

-continued

| | | | | | | | | | |
|---|---|---|---|---|---|---|---|---|---|
| 153 | H | H | H | H | H | H | −CH(CH₃)− | −CON(CH(CH₃)₂)₂ | |
| 154 | H | H | H | H | H | H | −CH(CH₃)− | −COOCH₂CH₂N(CH(CH₃)₂)₂ | |
| 155 | H | H | H | H | H | H | −CH(CH₃)− | −CON(CH₃)₂ | Melting point 105-111° C. |
| 156 | Br | H | Cl | H | H | H | −CH₂CH₂− | −COOCH₃ | |
| 157 | H | H | H | H | H | H | −CH(CH₃)− | −COOCH₂CH₂N(CH₃)₂ | |
| 158 | H | H | H | H | H | H | −CH(CH₃)− | −CONH−C₆H₄−NO₂ | |
| 159 | H | H | H | H | H | H | −CH(CH₃)− | −COOCH₂C(CH₃)₂N(CH₃)₂ | |
| 160 | H | H | H | H | H | H | −CH(CH₃)− | −COOCH(CH₃)CH₂N(CH₃)₂ | |
| 161 | H | H | H | H | H | H | −CH(CH₃)− | −COO(CH₂)₃N(CH₃)₂ | |
| 162 | Br | H | Cl | H | H | H | −CH₂CH₂− | −COOCH₃ | |
| 163 | H | H | H | H | H | H | −CH(CH₃)− | −CONH(CH₂)₃N(CH₃)₂ | |
| 164 | Br | H | Cl | H | H | H | −CH₂CH₂− | −COOC₂H₅ | |
| 165 | H | H | H | H | H | H | −CH(CH₃)− | −COO−(2,6-dimethylphenyl) | |
| 166 | H | H | H | H | H | H | −CH(CH₃)− | −COO−(2,4-dinitrophenyl) | |
| 167 | H | H | H | H | H | H | −CH(CH₃)− | −CON(C₅H₁₁n)₂ | |
| 168 | Br | H | Cl | H | H | H | −CH₂CH₂− | −COOC₃H₇n | |

-continued

| # | | | | | | | | |
|---|---|---|---|---|---|---|---|---|
| 169 | H | H | H | H | H | H | $-\underset{\underset{CH_3}{|}}{CH}-$ | $-CON\left(\underset{\phantom{x}}{\underset{\phantom{x}}{\bigcirc}}\right)_2$ |
| 170 | H | H | H | H | H | H | $-\underset{\underset{CH_3}{|}}{CH}-$ | $-CON(C_3H_7n)_2$ |
| 171 | H | H | H | H | H | H | $-\underset{\underset{CH_3}{|}}{CH}-$ | $-COO(CH_2)_{11}CH_3$ |
| 172 | Br | H | Cl | H | H | H | $-CH_2CH_2-$ | $-CONH_2$ |
| 173 | H | H | H | H | H | H | $-\underset{\underset{CH_3}{|}}{CH}-$ | $-CONH(CH_2)_{11}CH_3$ |
| 174 | H | H | H | H | H | H | $-\underset{\underset{CH_3}{|}}{CH}-$ | $-COOCH_2\!-\!\!\!\underset{O}{\bigcirc}$ |
| 175 | H | H | H | H | H | H | $-\underset{\underset{CH_3}{|}}{CH}-$ | $-COS(CH_2)_{11}CH_3$ |
| 176 | H | H | H | H | H | H | $-\underset{\underset{CH_3}{|}}{CH}-$ | $-CONH-CH_2\!-\!\!\!\underset{O}{\bigcirc}$ |
| 177 | H | H | H | H | H | H | $-\underset{\underset{CH_3}{|}}{CH}-$ | $-COOCH_2\underset{\underset{OH}{|}}{CH}-CH_2OH$ |
| 178 | Br | H | Cl | H | H | H | $-\underset{\underset{CH_3}{|}}{CH}-$ | $-COOCH_3$ |
| 179 | H | H | H | H | H | H | $-\underset{\underset{CH_3}{|}}{CH}-$ | $-COO(CH_2)_6CH_3$ |
| 180 | H | H | H | H | H | H | $-\underset{\underset{CH_3}{|}}{CH}-$ | $-COO(CH_2)_{15}CH_3$ |
| 181 | H | H | H | H | H | H | $-\underset{\underset{CH_3}{|}}{CH}-$ | $-COO(CH_2)_6OH$ |
| 182 | Br | H | Cl | H | H | H | $-\underset{\underset{CH_3}{|}}{CH}-$ | $-COOC_2H_5$ |
| 183 | H | H | H | H | H | H | $-\underset{\underset{CH_3}{|}}{CH}-$ | $-COO\overset{\overset{CH_3}{|}}{C}H(CH_2)_2\overset{\overset{CH_3}{|}}{C}HOH$ |
| 184 | H | H | H | H | H | H | $-\underset{\underset{CH_3}{|}}{CH}-$ | $-COO(CH_2)_5CH_3$ |
| 185 | H | H | H | H | H | H | $-\underset{\underset{CH_3}{|}}{CH}-$ | $-CONH(CH_2)_5CH_3$ |
| 186 | H | H | H | H | H | H | $-\underset{\underset{CH_3}{|}}{CH}-$ | $-COO\!-\!\!\!\bigcirc\!\!-OCH_3$ |

| No. | | | | | | | | | |
|---|---|---|---|---|---|---|---|---|---|
| 187 | H | H | H | H | H | H | —CH(CH₃)— | —CONHCH₂CH₂NHCH₂CH₂OH | |
| 188 | Br | H | Cl | H | H | H | —CH(CH₃)— | —COOC₃H₇iso | Melting point 66–68° C. |
| 189 | H | H | H | | H | H | —CH(CH₃)— | —COOCH₂CH₂N(morpholino) | |
| 190 | Br | H | Cl | H | H | H | —CH(CH₃)— | —CONHCH₃ | |
| 191 | Br | H | Cl | H | H | H | —CH(CH₃)— | —CONH₂ | |
| 192 | Br | H | Cl | H | H | H | —CH(CH₃)— | —CON(CH₃)₂ | |
| 193 | H | H | H | H | H | H | —CH(CH₃)— | —COOCH₂CH₂N(piperidino) | |
| 194 | H | H | H | H | H | H | —CH(CH₃)— | —COOCH₂CH₂-(2-pyridyl) | |
| 195 | H | H | H | H | H | H | —CH(CH₃)— | —COOCH₂CN | |
| 196 | H | H | H | H | H | H | —CH(CH₃)— | —CONH(CH₂)₃COOCH₃ | |
| 197 | H | H | H | H | H | H | —CH(CH₃)— | —COO—C(CH₃)₂—COOC₂H₅ | |
| 198 | Cl | H | Cl | H | H | H | —CH₂— | —COOH | |
| 199 | H | H | H | H | H | H | —CH(CH₃)— | —COOCH₂-(cyclohexyl) | |
| 200 | H | H | H | H | H | H | —CH(CH₃)— | —COOCH₂-(2-pyridyl) | |
| 201 | H | H | H | H | H | H | —CH(CH₃)— | —COOCH₂CH₂CN | |
| 202 | Cl | H | Cl | H | H | H | —CH₂— | —COOCH₂CH₂OCH₃ | Melting point 68–70° C. |

| | | | | | | | | |
|---|---|---|---|---|---|---|---|---|
| 203 | H | H | H | H | H | H | —CH—<br>\|<br>CH₃ | —COOCH₂—[tetrahydropyran-2-yl] |
| 204 | H | H | H | H | H | H | —CH—<br>\|<br>CH₃ | —COO—[pyridyl] |
| 205 | H | H | H | H | H | H | —CH—<br>\|<br>CH₃ | —CON—[imidazolyl] |
| 206 | H | H | H | H | H | H | —CH—<br>\|<br>CH₃ | —CON(CH₂CN)₂ |
| 207 | H | H | H | H | H | H | —CH—<br>\|<br>CH₃ | —CONH(CH₂)₁₇CH₃ |
| 208 | Cl | H | Cl | H | H | H | —CH₂— | —COOCH₃ |
| 209 | H | H | H | H | H | H | —CH—<br>\|<br>CH₃ | —COO(CH₂)₇CH₃ |
| 210 | H | H | H | H | H | H | —CH—<br>\|<br>CH₃ | —COO—[phenyl] |
| 211 | H | H | H | H | H | H | —CH—<br>\|<br>CH₃ | —COOCH₂CH₂—[phenyl] |
| 212 | Cl | H | Cl | H | H | H | —CH₂— | —COOC₂H₅ |
| 213 | H | H | H | H | H | H | —CH—<br>\|<br>CH₃ | —CONH(CH₂)₇CH₃ |
| 214 | H | H | H | H | H | H | —CH—<br>\|<br>CH₃ | —CONH—CH(CH₃)—[phenyl] |
| 215 | H | H | H | H | H | H | —CH—<br>\|<br>CH₃ | —COO(CH₂)₄CH₃ |
| 216 | H | H | H | H | H | H | —CH—<br>\|<br>CH₃ | —CONHCH₂CH₂—[phenyl] |
| 217 | H | H | H | H | H | H | —CH—<br>\|<br>CH₃ | —COOCH₂CH₂CH₂—[phenyl] |
| 218 | Cl | H | Cl | H | H | H | —CH₂— | COOC₃H₇iso | Melting point 60–63° C. |

-continued

| 219 | H | H | H | H | H | H | —CH(CH₃)— | —CON(CH₂CH₂)₂NH (morpholine-like, 7-membered with NH) | |
| 220 | Cl | H | Cl | H | H | H | —CH₂— | —CONH₂ | |
| 221 | H | H | H | H | H | H | —CH(CH₃)— | —CON< (piperidine ring) | |
| 222 | Cl | H | Cl | H | H | H | —CH(CH₃)— | —COOH | |
| 223 | H | H | H | H | H | H | —CH(CH₃)— | —CONHCH₂CH₂—N< (piperidine) | |
| 224 | H | H | H | H | H | H | —CH(CH₃)— | —COOCH₂—C≡CH | |
| 225 | H | H | H | H | H | H | —CH(CH₃)— | —COOCH₂CH₂(OCH₂CH₂)₃OH | |
| 226 | Cl | H | Cl | H | H | H | —CH(CH₃)— | —COOCH₂CH₂OCH₃ | |
| 227 | H | H | H | H | H | H | —CH(CH₃)— | —COOCH₂CH₂SCH₂CH₂OH | |
| 228 | Cl | H | Cl | H | H | H | —CH(CH₃)— | —COOC₂H₅ | |
| 229 | H | H | H | H | H | H | —CH(CH₃)— | —COSCH₂COOCH₃ | |
| 230 | Cl | H | Cl | H | H | H | —CH(CH₃)— | —COOC₃H₇n | |
| 231 | H | H | H | H | H | H | —CH(CH₃)— | —COS—C₆H₅ | |
| 232 | Cl | H | Cl | H | H | H | —CH(CH₃)— | —COOC₃H₇iso | Melting point 70–73° C. |
| 233 | H | H | H | H | H | H | —CH(CH₃)— | —CONH—C₆H₄—CH₃ | |
| 234 | H | H | H | H | H | H | —CH(CH₃)— | —COOCH₂CCl₃ | |
| 235 | H | H | H | H | H | H | —CH(CH₃)— | —COOCH₂—C(CH₂OH)₂—C₂H₅ | |

-continued

| | | | | | | | | |
|---|---|---|---|---|---|---|---|---|
| 236 | H | H | H | H | H | H | −CH(CH₃)− | −CON(OCH₃)(CH₃) |
| 237 | Cl | H | Cl | H | H | H | −CH(CH₃)− | −CON(CH₃)₂ |
| 238 | H | H | I | H | H | H | −CH(CH₃)− | −COOH |
| 239 | H | H | Br | H | H | CH₃ | −CH(CH₃)− | −COOH |
| 240 | Cl | H | Cl | H | H | H | −CH(CH₃)− | −CONHC₂H₅ |
| 241 | H | H | I | H | H | H | −CH(CH₃)− | −COOCH₂CH₂OCH₃ |
| 242 | H | H | Br | H | H | CH₃ | −CH(CH₃)− | −COOCH₂CH₂OCH₃ |
| 243 | Cl | H | Cl | H | H | H | −CH(CH₃)− | −CONH₂ |
| 244 | H | H | I | H | H | H | −CH(CH₃)− | −COOCH₃ |
| 245 | H | H | Br | H | H | CH₃ | −CH(CH₃)− | −COOCH₃ |
| 246 | H | H | I | H | H | H | −CH(CH₃)− | −COOC₂H₅ |
| 247 | H | H | I | H | H | H | −CH(CH₃)− | −CONHCH₃ |
| 248 | H | H | Br | H | H | CH₃ | −CH(CH₃)− | −CON(CH₃)₂ |
| 249 | H | H | Br | H | H | H | −CH(CH₃)− | −COOH |
| 250 | H | H | Br | H | H | H | −CH(CH₃)− | −COOCH₂CH₂OCH₃ |
| 251 | H | H | I | H | H | H | −CH(CH₃)− | −CON(CH₃)₂ |
| 252 | H | H | Br | H | H | H | −CH(CH₃)− | −COOCH₃ |
| 253 | H | H | Cl | H | H | CH₃ | −CH₂− | −COOCH₃ |
| 254 | H | H | Br | H | H | H | −CH(CH₃)− | −CONH₂ |

-continued

| | | | | | | | | |
|---|---|---|---|---|---|---|---|---|
| 255 | H | H | Cl | H | H | CH$_3$ | —CH$_2$— | —COOC$_2$H$_5$ |
| 256 | H | H | Br | H | H | H | —CH(CH$_3$)— | —CONHC$_2$H$_5$ |
| 257 | H | H | Cl | H | H | CH$_3$ | —CH$_2$— | —CONHCH$_3$ |
| 258 | H | H | H | H | H | H | —CH$_2$CH$_2$— | —COOH |
| 259 | H | H | Cl | H | H | H | —CH$_2$CH$_2$— | —COOC$_2$H$_5$ |
| 260 | H | H | Cl | H | H | CH$_3$ | —CH$_2$— | —CON(CH$_3$)$_2$ |
| 261 | H | H | H | H | H | H | —CH$_2$CH$_2$— | —COOCH$_2$CH$_2$OCH$_3$ |
| 262 | H | H | Cl | H | H | H | —CH$_2$CH$_2$— | —COOC$_3$H$_7$iso |
| 263 | H | H | Cl | H | H | CH$_3$ | —CH(CH$_3$)— | —COOH |
| 264 | H | H | H | H | H | H | —CH$_2$CH$_2$— | —COOCH$_3$ |
| 265 | H | H | Cl | H | H | CH$_3$ | —CH(CH$_3$)— | —COOCH$_3$ |
| 266 | H | H | H | H | H | H | —CH$_2$CH$_2$— | —COOC$_2$H$_5$ |
| 267 | H | H | Cl | H | H | CH$_3$ | —CH(CH$_3$)— | —COOC$_2$H$_5$ |
| 268 | H | H | H | H | H | H | —CH$_2$CH$_2$— | —COOC$_3$H$_7$n |
| 269 | H | H | Cl | H | H | CH$_3$ | —CH(CH$_3$)— | —COOC$_3$H$_7$iso |
| 270 | H | H | H | H | H | H | —CH$_2$CH$_2$— | —CONHC$_3$H$_7$iso |
| 271 | H | H | Cl | H | H | CH$_3$ | —CH(CH$_3$)— | —CONHCH$_3$ |
| 272 | H | H | Cl | H | H | H | —CH$_2$CH$_2$— | —CONHCH$_3$ |
| 273 | H | H | Cl | H | H | CH$_3$ | —CH(CH$_3$)— | —CON(CH$_3$)$_2$ |
| 274 | H | H | H | H | H | H | —CH$_2$CH$_2$— | —CON(CH$_3$)$_2$ |
| 275 | H | H | Cl | H | H | H | —CH$_2$CH$_2$— | —CON(CH$_3$)$_2$ |
| 276 | H | H | Cl | H | H | H | —CH$_2$CH$_2$— | —CONHC$_2$H$_5$ |
| 277 | H | H | H | H | H | H | —CH$_2$CH$_2$— | —CONHC$_2$H$_5$ |
| 278 | H | H | Cl | H | H | H | —CH$_2$CH$_2$— | —CONH$_2$ |
| 279 | H | H | H | H | H | H | —CH$_2$CH$_2$— | —CON(C$_2$H$_5$)$_2$ |
| 280 | H | H | Cl | H | H | H | —CH(CH$_3$)— | —COOH |

-continued

| | | | | | | | | | |
|---|---|---|---|---|---|---|---|---|---|
| 281 | H | H | H | H | H | H | —CH$_2$CH$_2$— | —CONH$_2$ | |
| 282 | H | H | Cl | H | H | H | —CH(CH$_3$)— | —COOCH$_2$CH$_2$OCH$_3$ | |
| 283 | H | H | H | H | H | H | —CH$_2$CH$_2$— | —COOCH$_2$CH$_2$OC$_2$H$_5$ | |
| 284 | H | H | Cl | H | H | H | —CH(CH$_3$)— | —COOCH$_3$ | |
| 285 | H | H | H | H | H | H | —CH$_2$CH$_2$— | —CON(CH$_3$)(CH$_2$CH$_2$OH) | |
| 286 | H | H | Cl | H | H | H | —CH(CH$_3$)— | —COOC$_2$H$_5$ | |
| 287 | H | H | Cl | H | H | H | —CH$_2$— | —COOH | Melting point 232–233° C. |
| 288 | H | H | Cl | H | H | H | —CH(CH$_3$)— | —COOC$_3$H$_7$n | |
| 289 | H | H | Cl | H | H | H | —CH$_2$— | —COOCH$_2$CH$_2$OCH$_3$ | Melting point 97–98° C. |
| 290 | H | H | Cl | H | H | H | —CH(CH$_3$)— | —CONHCH$_3$ | |
| 291 | H | H | Cl | H | H | H | —CH$_2$— | —COOCH$_3$ | Melting point 104–105.5° C. |
| 292 | H | H | Cl | H | H | H | —CH(CH$_3$)— | —CON(CH$_3$)$_2$ | |
| 293 | H | H | Cl | H | H | H | —CH$_2$— | —COOC$_2$H$_5$ | Melting point 116–117° C. |
| 294 | H | H | Cl | H | H | H | —CH(CH$_3$)— | —CONHC$_2$H$_5$ | |
| 295 | H | H | Cl | H | H | H | —CH$_2$— | —COOC$_3$H$_7$n | Melting point 108–109° C. |
| 296 | H | H | Cl | H | H | H | —CH(CH$_3$)— | —CON(C$_2$H$_5$)$_2$ | |
| 297 | H | H | Cl | H | H | H | —CH$_2$— | —CONHCH$_3$ | |
| 298 | H | H | Cl | H | H | H | —CH(CH$_3$)— | —CONH$_2$ | |
| 299 | H | H | Cl | H | H | H | —CH$_2$— | —CON(CH$_3$)$_2$ | Melting point 135–136° C. |
| 300 | H | H | Cl | H | H | H | —CH(CH$_3$)— | —COOCH$_2$CH$_2$OC$_2$H$_5$ | |
| 301 | H | H | Cl | H | H | H | —CH$_2$— | —CONH$_2$ | |
| 302 | H | H | Cl | H | H | H | —CH(CH$_3$)— | —CONH(CH$_2$)$_3$CH$_3$ | |
| 303 | H | H | Cl | H | H | H | —CH$_2$CH$_2$— | —COOH | |

-continued

| No. | | | | | | | | | |
|---|---|---|---|---|---|---|---|---|---|
| 304 | H | H | Cl | H | H | H | —CH$_2$CH$_2$— | —COOCH$_2$CH$_2$OCH$_3$ | |
| 305 | H | H | Cl | H | H | H | —CH$_2$CH$_2$— | —COOCH$_3$ | |
| 306 | H | H | Cl | H | H | H | —CH(CH$_3$)— | —CON(CH$_3$)CH$_2$CH$_2$OH | |
| 307 | H | H | H | H | H | CH$_3$ | —CH$_2$— | —COOCH$_3$ | Melting point 58–66° C. |
| 308 | H | H | H | H | H | CH$_3$ | —CH(CH$_3$)— | —COOH | |
| 309 | H | H | Cl | H | H | H | —CH(CH$_3$)— | —COOCH$_2$-(oxiranyl) | $n_D^{30} = 1.5734$ |
| 310 | H | H | H | H | H | CH$_3$ | —CH$_2$— | —CON(CH$_3$)$_2$ | |
| 311 | H | H | H | H | H | CH$_3$ | —CH(CH$_3$)— | —COOCH$_3$ | |
| 312 | H | H | H | H | H | CH$_3$ | —CH(CH$_3$)— | —COOC$_3$H$_7$iso | |
| 313 | H | H | H | H | H | CH$_3$ | —CH(CH$_3$)— | —CON(CH$_3$)$_2$ | |
| 314 | H | H | H | H | H | CH$_3$ | —CH(CH$_3$)— | —CONHCH$_3$ | |
| 315 | H | H | H | H | H | CH$_3$ | —CH(CH$_3$)— | —CON(C$_2$H$_5$)$_2$ | |
| 316 | H | H | H | H | H | CH$_3$ | —CH(CH$_3$)— | —CONH$_2$ | |
| 317 | H | H | H | H | H | H | —CH$_2$— | —C(=N-O-CH$_2$)  | |
| 318 | H | H | Cl | H | H | H | —CH(CH$_3$)— | " | |
| 319 | Br | H | Cl | H | H | H | —CH$_2$— | " | |
| 320 | H | H | H | H | H | CH$_3$ | —CH$_2$— | " | |
| 321 | Br | H | Cl | H | H | H | —CH$_2$CH$_2$— | " | |
| 322 | Cl | H | Cl | H | H | CH$_3$ | —CH$_2$— | " | |
| 323 | H | H | H | H | H | H | —CH$_2$CH$_2$— | " | |
| 324 | H | H | H | H | H | CH$_3$ | —CH$_2$CH$_2$— | " | |
| 325 | Br | H | Cl | H | H | H | —CH(CH$_3$)— | " | |
| 326 | H | H | Cl | H | H | H | —CH$_2$— | " | |
| 327 | H | H | H | H | H | H | —CH(CH$_3$)— | " | |

-continued

| No. | R₁ | R₂ | R₃ | R₄ | R₅ | R₆ | X + Y | |
|---|---|---|---|---|---|---|---|---|
| 328 | Cl | H | Cl | H | H | CH₃ | —CH₂CH₂— | " |
| 329 | H | H | H | H | H | CH₃ | —CH—<br>    \|<br>   CH₃ | 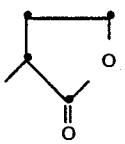 |
| 330 | H | H | Br | H | H | H | —CH₂— | " |
| 331 | Cl | H | Cl | H | H | CH₃ | —CH—<br>    \|<br>   CH₃ | " |
| 332 | H | H | Cl | H | H | H | —CH₂—CH₂— | " |
| 333 | H | H | Br | H | H | H | —CH₂—CH₂— | " |
| 334 | H | H | C₂H₅ | H | H | H | —CH₂— | " |
| 335 | H | H | Br | H | H | H | —CH—<br>    \|<br>   CH₃ | " |
| 336 | H | H | C₂H₅ | H | H | H | —CH₂CH₂— | " |
| 337 | Cl | H | Cl | H | H | H | —CH₂— | " |
| 338 | I | H | Cl | H | H | H | —CH₂— | " |
| 339 | I | H | Cl | H | H | H | —CH₂CH₂— | " |
| 340 | Cl | H | Cl | H | H | H | —CH₂CH₂— | " |
| 341 | H | H | C₂H₅ | H | H | H | —CH—<br>    \|<br>   CH₃ | " |
| 342 | Cl | H | Cl | H | H | H | —CH—<br>    \|<br>   CH₃ | " |
| 343 | I | H | Cl | H | H | H | —CH—<br>    \|<br>   CH₃ | " |

| Compound No. | R₁ | R₂ | R₃ | R₄ | R₅ | R₆ | X + Y | Physical constants °C. |
|---|---|---|---|---|---|---|---|---|
| 344 | H | H | H | H | H | H |  |  |
| 345 | H | H | Cl | H | H | H | " | 140–141.5° C. |
| 346 | Cl | H | Cl | H | H | H | " |  |
| 347 | H | H | H | H | H | CH₃ | " |  |
| 348 | H | H | Br | H | H | H | " |  |
| 349 | Br | H | Cl | H | H | H | " |  |
| 350 | H | H | Br | H | H | CH₃ | " |  |
| 351 | H | H | Cl | H | H | CH₃ | " |  |
| 352 | H | H | I | H | H | H | " |  |
| 353 | I | H | Cl | H | H | H | " |  |
| 354 | Cl | H | Cl | H | H | CH₃ | " |  |
| 355 | H | H | NO₂ | H | H | H | " |  |
| 356 | H | H | C₂H₅ | H | H | H | " |  |
| 357 | Cl | H | CH₃ | H | H | H | " |  |

| Compound No. | R₁ | R₂ | R₃ | R₄ | R₅ | R₆ | X | Y | Physical constants |
|---|---|---|---|---|---|---|---|---|---|
| 358 | H | H | H | H | H | CH₃ | —CH₂— | —COOC₂H₅ | $n_D^{22.5} = 1.5762$ |
| 359 | H | H | Cl | H | H | H | —CH₂— | —COOC₄H₉tert. | Melting point 63–69° C. |
| 360 | H | H | H | H | H | H | —CH₂— | —COOC₄H₉tert. | Melting point 68–70° C. |
| 361 | H | H | Cl | H | H | H | —CH₂— | —COOCH₂—C≡CH | Melting point 115–116° C. |
| 362 | H | H | Cl | H | H | H | —CH₂— | —COOC₃H₇iso | Melting point |

-continued

| | | | | | | | | | |
|---|---|---|---|---|---|---|---|---|---|
| 363 | H | H | Cl | H | H | H | —CH$_2$— | —COOCH$_2$CH$_2$OC$_2$H$_5$ | 147–148° C. Melting point 102–104° C. |
| 364 | H | H | Cl | H | H | H | —CH$_2$— | 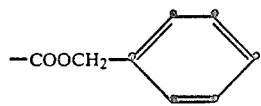 | Melting point 110–112° C. |
| 365 | H | H | Cl | H | H | H | —CH$_2$— | —COOCH$_2$—CH=CH$_2$ | Melting point 98–99° C. |
| 366 | H | H | Cl | H | H | H | —CH$_2$— | —COO(CH$_2$)$_{11}$CH$_3$ | Melting point 76–77° C. |
| 367 | H | H | Cl | H | H | H | —CH$_2$— | —COOC$_4$H$_9$sec. | Melting point 110–111° C. |
| 368 | H | H | H | H | H | H | —CH$_2$— | —COO(CH$_2$)$_7$CH$_3$ | $n_D^{24}$ = 1.5419 |
| 369 | H | H | Cl | H | H | H | —CH$_2$— | —COOC$_4$H$_9$n | Melting point 90.5–92° C. |
| 370 | H | H | H | H | H | H | 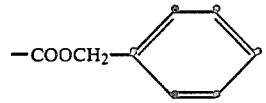 | —COOC$_2$H$_5$ | $n_D^{24}$ = 1.5600 |
| 371 | H | H | H | H | H | H | —CH$_2$— | —COO(CH$_2$)$_{11}$CH$_3$ | $n_D^{23}$ = 1.5232 |
| 372 | H | H | H | H | H | H | —CH$_2$— | —COOCH$_2$—CH=CH$_2$ | $n_D^{23}$ = 1.5885 |
| 373 | H | H | Cl | H | H | H | 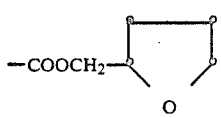 | —COOC$_2$H$_5$ | Melting point 57–58° C. |
| 374 | H | H | Cl | H | H | H | —CH$_2$— | —COO(CH$_2$)$_7$CH$_3$ | Melting point 87–88° C. |
| 375 | H | H | H | H | H | H | —CH$_2$— | —COOC$_4$H$_9$n | $n_D^{22}$ = 1.5642 |
| 376 | H | H | H | H | H | H | —CH$_2$— | —COOC$_4$H$_9$sec. | Oil (red) |
| 377 | H | H | Cl | H | H | H | —CH$_2$— | —COOCH$_2$CH$_2$Cl | Melting point 125–126° C. |
| 378 | H | H | H | H | H | H | —CH$_2$— | 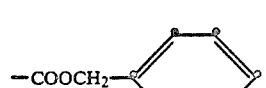 | $n_D^{23.5}$ = 1.6099 |
| 379 | H | H | Cl | H | H | H | —CH$_2$— | —COOCH$_2$—⟨furyl⟩ | Melting point 101–103° C. |
| 380 | H | H | Cl | H | H | H | —CH$_2$— | —COS(CH$_2$)$_7$CH$_3$ | Melting point 53–54° C. |
| 381 | H | H | H | H | H | H | —CH$_2$— | —COOCH$_2$CH$_2$Cl | Melting point 109–110° C. |
| 382 | I | H | Cl | H | H | H | —CH$_2$— | —COOC$_4$H$_9$tert. | Melting point 81–97° C. |
| 383 | I | H | Cl | H | H | H | —CH$_2$— | —COOC$_2$H$_5$ | Melting point 92–94° C. |
| 384 | I | H | Cl | H | H | H | —CH$_2$— | —COO(CH$_2$)$_{11}$CH$_3$ | Melting point 51–53° C. |
| 385 | I | H | Cl | H | H | H | —CH$_2$— | —COOCH$_3$ | Melting point 121–126° C. |
| 386 | I | H | Cl | H | H | H | —CH$_2$— | —COOCH$_2$CH$_2$Cl | Melting point 44–45° C. |
| 387 | I | H | Cl | H | H | H | —CH$_2$— | —COOCH$_2$—⟨Ph⟩ | Melting point 112–113° C. |
| 388 | I | H | Cl | H | H | H | —CH$_2$ | —COOC$_3$H$_7$n | Melting point 71–73° C. |

| | | | | | | | | | |
|---|---|---|---|---|---|---|---|---|---|
| 389 | H | H | H | H | H | CH$_3$ | $-\underset{\underset{CH_3}{\mid}}{\overset{\overset{CH_3}{\mid}}{C}}-$ | —COOC$_2$H$_5$ | Melting point 47–53° C. |
| 390 | H | H | H | H | H | H | —CH$_2$— | —COOC$_4$H$_9$iso | n$_D^{22}$ = 1.5632 |
| 391 | H | H | H | H | H | H | —CH$_2$— | —COOCH(CH$_3$)CH$_2$CH$_3$ | n$_D^{22}$ = 1.5391 |
| 392 | H | H | H | H | H | H | —CH$_2$— | —COOCH(CH$_3$)(CH$_2$)$_5$CH$_3$ | n$_D^{22}$ = 1.5342 |
| 393 | H | H | H | H | H | H | —CH$_2$— | —CONH(CH$_2$)$_{11}$CH$_3$ | Melting point 56–61° C. |
| 394 | H | H | H | H | H | H | —CH$_2$— | —CONHCH$_2$CH$_2$—N(morpholino) | Melting point 94–99° C. |
| 395 | H | H | H | H | H | H | —CH$_2$— | —CONHCH$_2$CH$_2$CH$_2$OH | Melting point 138–139° C. |
| 396 | H | H | H | H | H | H | —CH$_2$— | —CONH—C$_6$H$_{11}$ | Melting point 104–106° C. |
| 397 | H | H | H | H | H | H | —CH$_2$— | —CON(morpholino) | Melting point 99–103° C. |
| 398 | H | H | H | H | H | H | —CH$_2$— | —CONHCH$_2$CH$_2$N(C$_2$H$_5$)$_2$ | n$_D^{23}$ = 1.5686 |
| 399 | H | H | H | H | H | H | —CH$_2$— | —CON(CH$_2$CH$_2$OH)$_2$ | Melting point 144–146° C. |
| 400 | H | H | H | H | H | H | —CH$_2$— | —CONH(CH$_2$)$_3$N(CH$_3$)$_2$ | n$_D^{23}$ = 1.5766 |
| 401 | H | H | H | H | H | H | —CH$_2$— | —CON(CH$_3$)(C$_4$H$_9$n) | n$_D^{22}$ = 1.5840 |
| 402 | H | H | H | H | H | H | —CH$_2$— | —CONHCH$_2$—C$_6$H$_5$ · H$_2$O | Melting point 70.5–73.5° C. |
| 403 | H | H | H | H | H | H | —CH$_2$— | —CONHCH(CH$_2$CH$_3$)CH$_2$OH | Melting point 150–151° C. |
| 404 | H | H | H | H | H | H | —CH$_2$— | —CON(C$_4$H$_9$n)$_2$ · 2H$_2$O | Melting point 105–106° C. |

-continued

| No. | | | | | | | | | |
|---|---|---|---|---|---|---|---|---|---|
| 405 | H | H | H | H | H | H | —CH$_2$— | —CONHCH$_2$CH$_2$—N(piperidine) | $n_D^{26}$ = 1.5821 |
| 406 | H | H | H | H | H | H | —CH$_2$— | —CONH(CH$_2$)$_3$N(CH$_2$CH$_2$OH)$_2$ | Melting point 109–110° C. |
| 407 | H | H | H | H | H | H | —CH$_2$— | —CONHCH$_2$—CH=CH$_2$.H$_2$O | Melting point 71–75° C. |
| 408 | H | H | H | H | H | H | —CH$_2$— | —CONHCH$_2$-(tetrahydrofuryl).H$_2$O | Melting point 57–58° C. |
| 409 | H | H | H | H | H | H | —CH$_2$— | —CONH(CH$_2$)$_3$OC$_2$H$_5$ | Melting point 51–61° C. |
| 410 | H | H | H | H | H | H | —CH$_2$— | —CONHCH$_2$CH$_2$NHCH$_2$CH$_2$OH | Melting point 70–91° C. |
| 411 | H | H | Cl | H | H | H | —CH$_2$— | —CONH(CH$_2$)$_3$OC$_2$H$_5$ | Melting point 85–88° C. |
| 412 | H | H | Cl | H | H | H | —CH$_2$— | —CON(CH$_3$)(CH$_2$CH$_2$OH) | Melting point 187–189° C. |
| 413 | H | H | Cl | H | H | H | —CH$_2$— | —CON(CH$_2$CH$_2$OH)$_2$ | Melting point 177–179° C. |
| 414 | H | H | Cl | H | H | H | —CH$_2$— | —CON(morpholine) | Melting point 148–150° C. |
| 415 | H | H | Cl | H | H | H | —CH$_2$— | —CONHCH$_2$CH$_2$CH$_2$OH | Melting point 157–160° C. |
| 416 | H | H | Cl | H | H | H | —CH$_2$— | —CONHC$_4$H$_9$n.H$_2$O | Melting point 87–90° C. |
| 417 | H | H | Cl | H | H | H | —CH$_2$— | —CONHC$_2$H$_5$ | Melting point 94–98° C. |
| 418 | H | H | Cl | H | H | H | —CH$_2$— | —CONHCH$_2$—(phenyl).½H$_2$O | Melting point 146–149° C. |
| 419 | H | H | H | H | H | CH$_3$ | —CH$_2$— | —CONH$_2$ | Melting point 193–196° C. |
| 420 | H | H | H | H | H | H | —CH$_2$— | —CONHNH$_2$.H$_2$O | Melting point 121–124° C. |
| 421 | H | H | H | H | H | H | —CH$_2$— | —COONa.H$_2$O | Melting point 140–142° C. |
| 422 | H | H | H | H | H | H | —CH$_2$— | —COOK.H$_2$O | Melting point >200° C. |
| 423 | H | H | H | H | H | H | —CH$_2$— | —COO$^\ominus$HN(CH$_3$)$_3^\oplus$ | Melting point 176–178° C. |
| 424 | H | H | H | H | H | H | —CH$_2$— | —COO$^\ominus$HN(CH$_2$CH$_2$OH)$_3^\oplus$ | Melting point 97–98° C. |
| 425 | H | H | Cl | H | H | H | —CH$_2$— | —COOK.H$_2$O | Melting point >260° C. |
| 426 | H | H | Cl | H | H | H | —CH$_2$— | —COONa.H$_2$O | Melting point >260° C. |

-continued

| | | | | | | | | | |
|---|---|---|---|---|---|---|---|---|---|
| 427 | H | H | H | H | H | H | —CH$_2$— | —COO$^\ominus$H$\overset{\oplus}{N}$(C$_2$H$_5$)$_3$ | Melting point 255–257° C. (decomposition) |
| 428 | H | H | Cl | H | H | H | —CH$_2$— | —COO$^\ominus$$\overset{\oplus}{N}$H$_4$ | Melting point 227–228° C. (decomposition) |
| 429 | H | H | Cl | H | H | H | —CH$_2$— | —COO$^\ominus$H$\overset{\oplus}{N}$(CH$_2$CH$_2$OH)$_3$ | Melting point 132–156° C. (decomposition) |
| 430 | H | H | Cl | H | H | H | —CH(CH$_3$)— | —COO-(2-CH$_3$,4-CH$_3$-C$_6$H$_3$) | Melting point 120–122° C. |
| 431 | H | H | Cl | H | H | H | —CH$_2$— | —COOCH(CH$_3$)(CH$_2$)$_5$CH$_3$ | Melting point 65–67° C. |
| 432 | H | H | Cl | H | H | H | —CH$_2$— | —COOCH$_2$CH=CH—CH$_3$ | Melting point 100–102° C. |
| 433 | H | H | Cl | H | H | H | —CH$_2$— | —COOCH$_2$—C(CH$_3$)=CH$_2$ | Melting point 94–95° C. |
| 434 | H | H | Cl | H | H | H | —CH$_2$— | —COOCH$_2$CH$_2$OC$_3$H$_7$iso | Melting point 70–72° C. |
| 435 | H | H | Cl | H | H | H | —CH$_2$— | —COOCH$_2$CH$_2$—O—C$_6$H$_5$ | Melting point 79–80,5° C. |
| 436 | Br | H | Br | H | H | H | —CH$_2$— | —COOCH$_3$ | Melting point 143–145° C. |
| 437 | Br | H | Cl | H | H | H | —CH$_2$— | —COOC$_3$H$_7$iso | Melting point 71–73° C |
| 438 | Br | H | Br | H | H | H | —CH$_2$— | —COOC$_3$H$_7$iso | Melting point 47–51° C. |
| 439 | Cl | H | Cl | H | H | H | —CH$_2$— | —COOC$_4$H$_9$n | Melting point 42–43,5° C. |
| 440 | Br | H | Cl | H | H | H | —CH$_2$— | —COOC$_4$H$_9$n | Melting point ca. 28° C. |
| 441 | Cl | H | Cl | H | H | H | —CH$_2$— | —COO(CH$_2$)$_7$CH$_3$ | Melting point ca. 30° C. |
| 442 | Br | H | Cl | H | H | H | —CH$_2$— | —COO(CH$_2$)$_7$CH$_3$ | Melting point 41–42° C. |
| 443 | Br | H | Cl | H | H | H | —CH$_2$— | —COOCH(CH$_3$)(CH$_2$)$_5$CH$_3$ | Melting point 46–48° C. |
| 444 | Cl | H | Cl | H | H | H | —CH$_2$— | —COO(CH$_2$)$_{11}$CH$_3$ | Melting point 49–50° C. |
| 445 | Br | H | Cl | H | H | H | —CH$_2$— | —COO(CH$_2$)$_{11}$CH$_3$ | Melting point 50–52° C. |
| 446 | Cl | H | Cl | H | H | H | —CH$_2$— | —COOCH$_2$—C$_6$H$_5$ | Melting point 79–80° C. |
| 447 | Br | H | Cl | H | H | H | —CH$_2$— | —COOCH$_2$—C$_6$H$_5$ | Melting point 100–102° C. |
| 448 | Br | H | Br | H | H | H | —CH$_2$— | —COOCH$_2$—C$_6$H$_5$ | Melting point 101–104° C. |

-continued

| | | | | | | | | | |
|---|---|---|---|---|---|---|---|---|---|
| 449 | Br | H | Cl | H | H | H | —CH$_2$— | —COOCH$_2$CH$_2$OCH$_3$ | Melting point 68–70° C. |
| 450 | Cl | H | Cl | H | H | H | —CH$_2$— | —COOCH$_2$CH$_2$OC$_2$H$_5$ | Melting point 81–82° C. |
| 451 | Br | H | Cl | H | H | H | —CH$_2$— | —COOCH$_2$CH$_2$OC$_2$H$_5$ | Melting point 71–72° C. |
| 452 | Br | H | Cl | H | H | H | —CH$_2$— | —COOCH$_2$CH$_2$OC$_3$H$_7$iso | n$_D^{25}$ = 1.5763 |
| 453 | Br | H | Cl | H | H | H | —CH$_2$— | —COOCH$_2$CH$_2$O—C$_6$H$_5$ | Melting point 80–82° C. |
| 454 | Cl | H | Cl | H | H | H | —CH$_2$— | —COOCH$_2$-(tetrahydrofuran-2-yl) | Melting point 77–78° C. |
| 455 | Br | H | Cl | H | H | H | —CH$_2$— | —COOCH$_2$-(tetrahydrofuran-2-yl) | Melting point 79–80° C. |
| 456 | Cl | H | Cl | H | H | H | —CH$_2$— | —COOCH$_2$CH=CH$_2$ | Melting point 72–73° C. |
| 457 | Br | H | Cl | H | H | H | —CH$_2$— | —COOCH$_2$CH=CH$_2$ | Melting point 66–68,5° C. |
| 458 | Br | H | Br | H | H | H | —CH$_2$— | —COOCH$_2$CH=CH$_2$ | Melting point 78–79° C. |
| 459 | Br | H | Cl | H | H | H | —CH$_2$— | —COOCH$_2$CH=CH—CH$_3$ | Melting point 60–64° C. |
| 460 | Cl | H | Cl | H | H | H | —CH$_2$— | —COOCH$_2$—C(CH$_3$)=CH$_2$ | Melting point 62–65° C. |
| 461 | Br | H | Cl | H | H | H | —CH$_2$— | —COOCH$_2$—C(CH$_3$)=CH$_2$ | Melting point 62–64° C. |
| 462 | Br | H | Cl | H | H | H | —CH$_2$— | —COO—C$_6$H$_4$(H) | Melting point 52–54° C. |
| 463 | H | H | Cl | H | H | H | —CH(CH$_3$)— | —COOC$_3$H$_7$iso | n$_D^{24}$ = 1.5642 |
| 464 | H | H | Cl | H | H | H | —CH(CH$_3$)— | —COO(CH$_2$)$_7$CH$_3$ | n$_D^{23}$ = 1.5356 |
| 465 | H | H | Cl | H | H | H | —CH(CH$_3$)— | —COOCH(CH$_3$)(CH$_2$)$_5$CH$_3$ | n$_D^{25}$ = 1.5370 |
| 466 | H | H | Cl | H | H | H | —CH(CH$_3$)— | —COO(CH$_2$)$_{11}$CH$_2$ | Melting point 54–55° C. |
| 467 | H | H | Cl | H | H | H | —CH(CH$_3$)— | —COOCH$_2$—C$_6$H$_5$ | Melting point 57–59° C. |
| 468 | H | H | Cl | H | H | H | —CH(CH$_3$)— | —COOCH$_2$CH$_2$OC$_3$H$_7$iso | n$_D^{32}$ = 1.5403 |
| 469 | H | H | Cl | H | H | H | —CH(CH$_3$)— | —COOCH$_2$CH$_2$O—C$_6$H$_5$ | n$_D^{29}$ = 1.5962 |

-continued

| No. | | | | | | | R | R' | |
|---|---|---|---|---|---|---|---|---|---|
| 470 | H | H | Cl | H | H | H | —CH(CH₃)— | —COOCH₂CH=CH₂ | Melting point 40–41° C. |
| 471 | H | H | Cl | H | H | H | —CH(CH₃)— | —COOCH₂CH=CH—CH₃ | Melting point 39–40° C. |
| 472 | H | H | Cl | H | H | H | —CH(CH₃)— | —COOCH₂—C(CH₃)=CH₂ | Melting point 62–63° C. |
| 473 | H | H | Cl | H | H | H | —CH(CH₃)— | —COO-cyclohexyl | $n_D^{30} = 1.5677$ |
| 474 | Br | H | Cl | H | H | H | —CH(CH₃)— | —COO(CH₂)₇CH₃ | $n_D^{28} = 1.5439$ |
| 475 | Cl | H | Cl | H | H | H | —CH(CH₃)— | —COOCH(CH₃)(CH₂)₅CH₃ | $n_D^{25} = 1.5408$ |
| 476 | Br | H | Cl | H | H | H | —CH(CH₃)— | —COOCH(CH₃)(CH₂)₅CH₃ | $n_D^{25} = 1.5527$ |
| 477 | Br | H | Cl | H | H | H | —CH(CH₃)— | —COO(CH₂)₁₁CH₃ | $n_D^{30} = 1.5347$ |
| 478 | Br | H | Cl | H | H | H | —CH(CH₃)— | —COOCH₂—phenyl | Melting point 55–56° C. |
| 479 | Br | H | Cl | H | H | H | —CH(CH₃)— | —COOCH₂-furyl | $n_D^{30} = 1.5586$ |
| 480 | Br | H | Cl | H | H | H | —CH(CH₃)— | —COOCH₂CH₂OC₃H₇iso | $n_D^{28} = 1.5642$ |
| 481 | Br | H | Cl | H | H | H | —CH(CH₃)— | —COOCH₂CH₂O-phenyl | $n_D^{20} = 1.6031$ |
| 482 | Br | H | Cl | H | H | H | —CH(CH₃)— | —COOCH₂CH=CH₂ | Melting point 55–56° C. |
| 483 | Cl | H | Cl | H | H | H | —CH(CH₃)— | —COOCH₂CH=CH—CH₃ | Melting point 38–39° C. |
| 484 | Br | H | Cl | H | H | H | —CH(CH₃)— | —COOCH₂CH=CH—CH₃ | Melting point 38–40° C. |
| 485 | Br | H | Cl | H | H | H | —CH(CH₃)— | —COOCH₂C(CH₃)=CH₂ | $n_D^{28} = 1.5824$ |

-continued

| | | | | | | | | |
|---|---|---|---|---|---|---|---|---|
| 486 | H | H | Cl | H | H | H | —CH$_2$— | —COO—<phenyl> | Melting point 165–170° C. |
| 487 | H | H | Cl | H | H | H | —CH$_2$— | —COO—<phenyl>—CH$_3$ | Melting point 143–145° C. |
| 488 | H | H | Cl | H | H | H | —CH$_2$— | —COO—<phenyl with CH$_3$> | Melting point 111–116° C. |
| 489 | H | H | Cl | H | H | H | —CH$_2$— | —COO—<phenyl with CH$_3$, CH$_3$> | Melting point 108–119° C. |
| 490 | H | H | Cl | H | H | H | —CH—CH$_3$ | —COO—<phenyl> | Melting point 102–105° C. |
| 491 | H | H | Cl | H | H | H | —CH$_2$— | —COOCH$_2$CH(CH$_3$)CH$_2$CH$_3$ | Melting point 65–70° C. |
| 492 | H | H | H | H | H | H | —CH$_2$— | —COOCH$_2$—C(CH$_3$)H(CH$_2$)$_2$CH$_3$ | |
| 493 | H | H | Cl | H | H | H | —CH$_2$— | —COO—<phenyl H> | Melting point 112–113° C. |
| 494 | H | H | Cl | H | H | H | —CH$_2$— | —COOCH$_2$CH(CH$_3$)—CH$_3$ | Melting point 113–114° C. |
| 495 | H | H | H | H | H | H | —CH$_2$— | —COO(CH$_2$)$_2$CH(OCH$_3$)CH$_3$ | Oil, n$_D^{23}$ = 1.5732 |
| 496 | H | H | H | H | H | H | —CH$_2$— | —COOCH$_2$CH$_2$OCH$_2$CH$_2$O(CH$_2$)$_3$CH$_3$ | |
| 497 | H | H | H | H | H | H | —CH$_2$— | —COS(CH$_2$)$_3$CH$_3$ | |
| 498 | H | H | H | H | H | H | —CH$_2$— | —COO—<phenyl H> | |
| 499 | H | H | H | H | H | H | —CH$_2$— | —COO(CH$_2$)$_4$CH$_3$ | |
| 500 | H | H | H | H | H | H | —CH$_2$— | —COS(CH$_2$)$_7$CH$_3$ | Oil; n$_D^{22}$ = 1.5697 |
| 501 | H | H | Cl | H | H | H | —CH$_2$— | —COOCH$_2$—CH(CH$_3$)(CH$_2$)$_2$CH$_3$ | |
| 502 | H | H | Cl | H | H | H | —CH$_2$— | —COS(CH$_2$)$_3$CH$_3$ | |
| 503 | H | H | H | H | H | H | —CH$_2$— | —COOCH$_2$CH=CH—CH$_3$ | Oil; n$_D^{22}$ = 1.5833 |
| 504 | H | H | H | H | H | H | —CH$_2$— | —COOCH$_2$—CH(C$_2$H$_5$)—C$_2$H$_5$ | |
| 505 | H | H | Cl | H | H | H | —CH$_2$— | —COOCH$_2$CH$_2$OCH$_2$CH$_2$O(CH$_2$)$_3$CH$_3$ | Melting point 39–41° C. |

-continued

| | | | | | | | | | |
|---|---|---|---|---|---|---|---|---|---|
| 506 | H | H | Cl | H | H | H | —CH$_2$— | —COO(CH$_2$)$_2$CH(OCH$_3$)CH$_3$ | Melting point 72–73° C. |
| 507 | H | H | Cl | H | H | H | —CH$_2$— | —COO(CH$_2$)$_4$CH$_3$ | Melting point 78–79° C. |
| 508 | H | H | Cl | H | H | H | —CH$_2$— | —COOCH(C$_2$H$_5$)—(CH$_2$)$_2$CH$_3$ | |
| 509 | H | H | H | H | H | H | —CH$_2$— | —COOCH$_2$CH$_2$OC$_3$H$_7$-iso | Oil; n$_D^{22}$ = 1.5546 |
| 510 | H | H | Cl | H | H | H | —CH$_2$— | —COO(CH$_2$)$_{13}$CH$_3$ | Melting point 75–76° C. |
| 511 | H | H | H | H | H | H | —CH$_2$— | —COOCH(C$_2$H$_5$)—C$_2$H$_5$ | |
| 512 | H | H | H | H | H | H | —CH$_2$— | —COO—(2-methylcyclohexyl) | Melting point 29–31° C. |
| 513 | H | H | Cl | H | H | H | —CH$_2$— | —COOCH$_2$—CH(C$_2$H$_5$)—C$_2$H$_5$ | |
| 514 | H | H | H | H | H | H | —CH$_2$— | —COOCH$_2$CH$_2$OCH$_2$CH$_2$OC$_2$H$_5$ | |
| 515 | H | H | H | H | H | H | —CH$_2$— | —COOCH$_2$CH$_2$O—(phenyl) | Melting point 80–81° C. |
| 516 | H | H | Cl | H | H | H | —CH$_2$— | —COOCH(C$_2$H$_5$)—C$_2$H$_5$ | |
| 517 | H | H | H | H | H | H | —CH$_2$— | —COOCH(CH$_3$)CH$_2$CH(CH$_3$)—CH$_3$ | |
| 518 | H | H | H | H | H | H | —CH$_2$— | —COO(CH$_2$)$_{13}$CH$_3$ | |
| 519 | H | H | H | H | H | H | —CH$_2$— | —COOCH$_2$CH$_2$O(CH$_2$)$_3$CH$_3$ | |
| 520 | H | H | Cl | H | H | H | —CH$_2$— | —COOCH$_2$CH$_2$OCH$_2$CH$_2$OC$_2$H$_5$ | Melting point 42–43° C. |
| 521 | H | H | H | H | H | H | —CH$_2$— | —COOCH$_2$—CH(CH$_3$)—C$_2$H$_5$ | |
| 522 | H | H | Cl | H | H | H | —CH$_2$— | —COOCH(CH$_3$)CH$_2$CH(CH$_3$)—CH$_3$ | Melting point 63–64° C. |
| 523 | H | H | H | H | H | H | —CH$_2$— | —COSCH(CH$_3$)—C$_2$H$_5$ | |
| 524 | H | H | Cl | H | H | H | —CH$_2$— | —COO—(2-methylcyclohexyl) | Melting point 98–101° C. |
| 525 | H | H | H | H | H | H | —CH$_2$— | —COOC(CH$_3$)(C$_2$H$_5$)(C$_2$H$_5$) | |
| 526 | H | H | H | H | H | H | —CH$_2$— | —COOCH$_2$—C(CH$_3$)=CH$_2$ | Oil; n$_D^{22}$ = 1.5805 |

| | | | | | | | | | |
|---|---|---|---|---|---|---|---|---|---|
| 527 | H | H | H | H | H | H | —CH$_2$— | —COOC(CH$_3$)$_2$—CH=CH$_2$ | Oil; n$_D^{22}$ = 1.5793 |
| 528 | H | H | H | H | H | H | —CH$_2$— | —COOCH$_2$CH$_2$OCH$_2$CH$_2$OCH$_3$ | |
| 529 | H | H | Cl | H | H | H | —CH$_2$— | —COOC(CH$_3$)(C$_2$H$_5$)$_2$ | |
| 530 | H | H | Cl | H | H | H | —CH$_2$— | —COO(CH$_2$)$_{10}$CH$_3$ | Melting point 70–71° C. |
| 531 | H | H | Cl | H | H | H | —CH$_2$— | —COOCH$_2$—CH(CH$_3$)—C$_2$H$_5$ | Melting point 78–79° C. |
| 532 | H | H | H | H | H | H | —CH$_2$— | —COO-(cyclohexyl-CH$_3$) | Melting point 40–42° C. |
| 533 | H | H | H | H | H | H | —CH$_2$— | —COO(CH$_2$)$_6$CH$_3$ | |
| 534 | H | H | H | H | H | H | —CH$_2$— | —COOC(CH$_3$)$_2$—C$_2$H$_5$ | |
| 535 | H | H | Cl | H | H | H | —CH$_2$— | —COOCH$_2$CH$_2$O(CH$_2$)$_3$CH$_3$ | Melting point 69–70° C. |
| 536 | H | H | Cl | H | H | H | —CH$_2$— | —COSCH(CH$_3$)—C$_2$H$_5$ | Melting point 55–56° C. |
| 537 | H | H | Cl | H | H | H | —CH$_2$— | —COOC(CH$_3$)$_2$—CH=CH$_2$ | Melting point 83–87° C. |
| 538 | H | H | H | H | H | H | —CH$_2$— | —COSCH$_3$ | Melting point 41–44° C. |
| 539 | H | H | Cl | H | H | H | —CH$_2$— | —COOCH$_2$CH$_2$OCH$_2$CH$_2$OCH$_3$ | Oil; n$_D^{23}$ = 1.5633 |
| 540 | H | H | Cl | H | H | H | —CH$_2$— | —COSCH$_3$ | Melting point 89–91° C. |
| 541 | H | H | Cl | H | H | H | —CH$_2$— | —COOC(CH$_3$)$_2$—C$_2$H$_5$ | |
| 542 | H | H | H | H | H | H | —CH$_2$— | —COO(CH$_2$)$_{10}$CH$_3$ | |
| 543 | H | H | Cl | H | H | H | —CH$_2$— | —COO(CH$_2$)$_6$CH$_3$ | Melting point 74–76° C. |
| 544 | H | H | H | H | H | H | —CH$_2$— | —COOCH(CH$_3$)—CH(CH$_3$)—CH$_3$ | |
| 545 | H | H | Cl | H | H | H | —CH$_2$— | —COO-(cyclohexyl-CH$_3$) | Melting point 103–105° C. |
| 546 | H | H | H | H | H | H | —CH$_2$— | —COSC(CH$_3$)$_3$ | |
| 547 | H | H | Cl | H | H | H | —CH$_2$— | —COS(CH$_2$)$_{11}$CH$_3$ | |
| 548 | H | H | Cl | H | H | H | —CH$_2$— | —COS(CH$_2$)$_9$CH$_3$ | |
| 549 | H | H | Cl | H | H | H | —CH$_2$— | —COO(CH$_2$)$_9$CH$_3$ | Melting point |

-continued

| | | | | | | | | | |
|---|---|---|---|---|---|---|---|---|---|
| | | | | | | | | | 73-74° C. |
| 550 | H | H | H | H | H | H | —CH$_2$— | —COOCH((CH$_2$)$_4$CH$_3$)CH$_3$ | |
| 551 | H | H | Cl | H | H | H | —CH$_2$— | —COOCH(C$_3$H$_7$-n)—C≡CH | Melting point 81–82° C. |
| 552 | H | H | H | H | H | H | —CH$_2$— | —COOCH(C$_5$H$_{11}$-n)—CH=CH$_2$ | |
| 553 | H | H | Cl | H | H | H | —CH$_2$— | —COOCH(CH$_3$)—CH(CH$_3$)—CH$_3$ | |
| 554 | H | H | Cl | H | H | H | —CH$_2$— | —COSC(CH$_3$)$_3$ | |
| 555 | H | H | H | H | H | H | —CH$_2$— | —COOCH(CH$_3$)—C≡CH | Oil; n$_D^{23}$ = 1.5837 |
| 556 | H | H | H | H | H | H | —CH$_2$— | —COS(CH$_2$)$_{11}$CH$_3$ | |
| 557 | H | H | H | H | H | H | —CH$_2$— | —COOCH$_2$—C(CH$_3$)$_3$ | |
| 558 | H | H | H | H | H | H | —CH$_2$— | —COSC$_2$H$_5$ | |
| 559 | H | H | Cl | H | H | H | —CH$_2$— | —COOCH$_2$—C(CH$_3$)$_3$ | |
| 560 | H | H | Cl | H | H | H | —CH$_2$— | —COSC$_3$H$_7$-n | |
| 561 | H | H | H | H | H | H | —CH$_2$— | —COO(CH$_2$)$_9$CH$_3$ | |
| 562 | H | H | Cl | H | H | H | —CH$_2$— | —COOCH(CH$_3$)(CH$_2$)$_4$CH$_3$ | |
| 563 | H | H | H | H | H | H | —CH$_2$— | —COO(CH$_2$)$_2$CH(CH$_3$)—CH$_3$ | |
| 564 | H | H | H | H | H | H | —CH$_2$— | —COOCH(C$_2$H$_5$)(CH$_2$)$_3$CH$_3$ | |
| 565 | H | H | Cl | H | H | H | —CH$_2$— | —COO(CH$_2$)$_8$CH$_3$ | Melting point 78–79° C. |
| 566 | H | H | H | H | H | H | —CH$_2$— | —COSCH$_2$CH(CH$_3$)CH$_3$ | |
| 567 | H | H | Cl | H | H | H | —CH$_2$— | —COSC$_2$H$_5$ | |
| 568 | H | H | H | H | H | H | —CH$_2$— | —COO(CH$_2$)$_8$CH$_3$ | Oil; n$_D^{24}$ = 1.5436 |
| 569 | H | H | Cl | H | H | H | —CH$_2$— | —COOCH$_2$—CH(C$_2$H$_5$)(CH$_2$)$_3$CH$_3$ | Melting point 45–47° C. |
| 570 | H | H | Cl | H | H | H | —CH$_2$— | —COSCH$_2$CH(CH$_3$)—CH$_3$ | |
| 571 | H | H | H | H | H | H | —CH$_2$— | —COS(CH$_2$)$_9$CH$_3$ | |
| 572 | H | H | Cl | H | H | H | —CH$_2$— | —COO(CH$_2$)$_2$CH(CH$_3$)—CH$_3$ | Melting point 72–74° C. |

-continued

| | | | | | | | | | |
|---|---|---|---|---|---|---|---|---|---|
| 573 | H | H | Cl | H | H | H | —CH$_2$— | —COOCH((CH$_2$)$_3$CH$_3$)C$_2$H$_5$ | |
| 574 | H | H | H | H | H | H | —CH$_2$— | —COO(CH$_2$)$_5$CH$_3$ | |
| 575 | H | H | H | H | H | H | —CH$_2$— | —COOCH((CH$_2$)$_2$CH$_3$)C$_3$H$_7$-n | |
| 576 | H | H | H | H | H | H | —CH$_2$— | —COS(CH$_2$)$_4$CH$_3$ | |
| 577 | H | H | H | H | H | H | —CH$_2$— | —COSC$_3$H$_7$-iso | |
| 578 | H | H | H | H | H | H | —CH$_2$— | —COOCH$_2$CH(C$_2$H$_5$)—(CH$_2$)$_3$CH$_3$ | |
| 579 | H | H | Cl | H | H | H | —CH$_2$— | —COOCH((CH$_2$)$_2$CH$_3$)C$_3$H$_7$-n | |
| 580 | H | H | Cl | H | H | H | —CH$_2$— | —COS(CH$_2$)$_5$CH$_3$ | |
| 581 | H | H | Cl | H | H | H | —CH$_2$— | —COS(CH$_2$)$_4$CH$_3$ | Oil; n$_D^{23}$ = 1.5990 |
| 582 | H | H | Cl | H | H | H | —CH$_2$— | —COO(CH$_2$)$_5$CH$_3$ | Melting point 71–72° C. |
| 583 | H | H | Cl | H | H | H | —CH$_2$— | —COSC$_3$H$_7$-iso | Melting point 62–64° C. |
| 584 | H | H | Cl | H | H | H | —CH$_2$— | —COOCH(C$_2$H$_5$)—CH$_2$CH(CH$_3$)C$_2$H$_5$ | |
| 585 | H | H | H | H | H | H | —CH$_2$— | —COOCH(C$_3$H$_7$-iso)—C$_3$H$_7$-iso | |
| 586 | H | H | H | H | H | H | —CH$_2$— | —COOCH(CH$_3$)—(CH$_2$)$_3$CH$_3$ | Oil; n$_D^{23}$ = 1.5531 |
| 587 | H | H | Cl | H | H | H | —CH$_2$— | —COOCH(C$_5$H$_{11}$-n)—CH=CH$_2$ | |
| 588 | H | H | H | H | H | H | —CH$_2$ | —COOCH(C$_2$H$_5$)—(CH$_2$)$_2$CH$_3$ | |
| 589 | H | H | H | H | H | H | —CH$_2$— | —COSC$_3$H$_7$-n | |
| 590 | H | H | Cl | H | H | H | —CH$_2$— | —COOCH(CH$_3$)—(CH$_2$)$_3$CH$_3$ | Melting point 68–71° C. |
| 591 | H | H | H | H | H | H | —CH$_2$— | —COOCHCH$_2$CH(C$_2$H$_5$)(CH$_3$)C$_2$H$_5$ | |
| 592 | H | H | Cl | H | H | H | —CH$_2$— | —COOCH(C$_3$H$_7$-iso)—C$_3$H$_7$-iso | |
| 593 | H | H | H | H | H | H | —CH$_2$— | —COS(CH$_2$)$_5$CH$_3$ | |
| 594 | H | H | H | H | H | H | —CH$_2$— | —COO(CH$_2$)$_9$—CH=CH$_2$ | |
| 595 | H | H | H | H | H | H | —CH$_2$— | —COOCH(C$_3$H$_7$-n)—C≡CH | |
| 596 | H | H | Cl | H | H | H | —CH$_2$— | —COOCH(CH$_3$)—C≡CH | Melting point 97–100° C. |
| 597 | H | H | H | H | H | H | —CH$_2$— | —COOC(CH$_3$)(C$_2$H$_5$)—C≡CH | |
| 598 | H | H | Cl | H | H | H | —CH$_2$— | —COO(CH$_2$)$_9$—CH=CH$_2$ | |

-continued

| | | | | | | | | |
|---|---|---|---|---|---|---|---|---|
| 599 | H | H | Cl | H | H | H | —CH$_2$— | —COO—C(CH$_3$)(CH$_3$)—C≡CH |
| 600 | H | H | H | H | H | H | —CH$_2$— | —COO—C(CH$_3$)(CH$_3$)—C≡CH |
| 601 | H | H | Cl | H | H | H | —CH$_2$— | —COO—C(CH$_3$)(C$_2$H$_5$)—C≡CH |
| 602 | H | H | Cl | H | H | H | —CH$_2$— | —COO—CH(CH$_3$)—CH(CH$_3$)—C$_2$H$_5$   Melting point 71–73° C. |

Formulation Examples for Liquid Active Substances of the Formula I (%=Per Cent by Weight)

2. Emulsion Concentrations

| | a) | b) | c) |
|---|---|---|---|
| Active substance from Table 1 | 25% | 40% | 50% |
| Ca dodecylbenzenesulfonate | 5% | 8% | 6% |
| Castor oil polyethylene glycol ether (36 mols of ethylene oxide) | 5% | — | — |
| Tributylphenol polyethylene glycol ether (30 mols of ethylene oxide) | — | 12% | 4% |
| Cyclohexanone | — | 15% | 20% |
| Xylene mixture | 65% | 25% | 20% |

Emulsions of any desired concentration can be prepared from such concentrates by dilution with water.

3. Solutions

| | a) | b) | c) | d) |
|---|---|---|---|---|
| Active substance from Table 1 | 80% | 10% | 5% | 95% |
| Ethylene glycol monomethyl ether | 20% | — | — | — |
| Polyethylene glycol molecular weight 400 | — | 70% | — | — |
| N-Methyl-2-pyrrolidone | — | 20% | — | — |
| Epoxidised coconut oil | — | — | 1% | 5% |
| Benzine (boiling range 160–190° C.) | — | — | 94% | — |

The solutions are suitable for application in the form of very small drops.

4. Granules

| | a) | b) |
|---|---|---|
| Active substance from Table 1 | 5% | 10% |
| Kaolin | 94% | — |
| Highly disperse silicic acid | 1% | — |
| Attapulgite | — | 90% |

The active substance is dissolved in methylene chloride, the solution is sprayed onto the carrier and the solvent is then evaporated off in vacuo.

5. Dusts

| | a) | b) |
|---|---|---|
| Active substance from Table 1 | 2% | 5% |
| Highly disperse silicic acid | 1% | 5% |
| Talc | 97% | — |
| Kaolin | — | 90% |

Ready-to-use dusts are obtained by intimate mixing of the carriers with the active substance.

Formulation Examples for Solid Active Substances of the Formula I (%=Per Cent by Weight)

6. Wettable Powders

| | a) | b) | c) |
|---|---|---|---|
| Active substance from Table 1 | 25% | 50% | 75% |
| Na Lignin-sulfonate | 5% | 5% | — |
| Na Lauryl-sulfate | 3% | — | 5% |
| Na diisobutylnaphthalenesulfonate | — | 6% | 10% |
| Octylphenol polyethylene glycol ether (7–8 mols of ethylene oxide) | — | 2% | — |
| Highly disperse silicic acid | 5% | 10% | 10% |
| Kaolin | 62% | 27% | — |

The active substance is mixed thoroughly with the adjuvants and the mixture is ground well in a suitable mill. Wettable powders which can be diluted with water to give suspension of any desired concentration are obtained.

7. Emulsion Concentrate

| | |
|---|---|
| Active substance from Table 1 | 10% |
| Octylphenol polyethylene glycol ether (4–5 mols of ethylene oxide) | 3% |
| Ca dodecylbenzenesulfonate | 3% |
| Castor oil polyglycol ether (35 mols of ethylene oxide) | 4% |
| Cyclohexanone | 30% |
| Xylene mixture | 50% |

Emulsions of any desired concentration can be prepared from this concentrate by dilution with water.

8. Dusts

| | a) | b) |
|---|---|---|
| Active substance from Table 1 | 5% | 8% |
| Talc | 95% | — |

-continued

|  | a) | b) |
|---|---|---|
| Kaolin | — | 92% |

Ready-to-use dusts are obtained by mixing the active substance with the carriers and grinding the mixture in a suitable mill.

9. Extruded Granules

| Active substance from Table 1 | 10% |
|---|---|
| Na Lignin-sulfonate | 2% |
| Carboxymethylcellulose | 1% |
| Kaolin | 87% |

The active substance is mixed with the adjuvants and the mixture is ground and moistened with water. This mixture is extruded and then dried in a stream of air.

10. Coated Granules

| Active substance from Table 1 | 3% |
|---|---|
| Polyethylene glycol (molecular weight 200) | 3% |
| Kaolin | 94% |

The finely ground active substance is uniformly applied to the kaolin, moistened with polyethylene glycol, in a mixer. Dust-free coated granules are obtained in this manner.

11. Suspension Concentrate

| Active substance from Table 1 | 40% |
|---|---|
| Ethylene glycol | 10% |
| Nonylphenol polyethylene glycol ether (15 mols of ethylene oxide) | 6% |
| Na Lignin-sulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is intimately mixed with the adjuvants. A suspension concentrate from which suspensions of any desired concentration can be prepared by dilution with water is thus obtained.

Biological Examples

EXAMPLE 12

Test With Antidote and Herbicide on Wheat

Wheat seeds are sown in plastic pots containing 0.5 liter of garden soil in a greenhouse. After emergence of the plants to the 2- to 3-leaf stage, the substance to be tested as an antidote is applied as a tank mixture together with the herbicide 2-propinyl 2-[4-(3,5-dichloropyridyl-2-oxy)-phenoxy]-propionate.

20 days after the application, the protective action of the antidote is rated in per cent. The plants treated with the herbicide by itself and the completely untreated controls serve as references. The results are shown in the following tables:

TABLE 2

| | Amounts applied: Herbicide 0.5 kg/ha Antidote 0.5 kg/ha |
|---|---|
| Compound No. | Relative protective action in percent |
| 1 | 50 |
| 3 | 50 |

TABLE 3

| | Amounts applied: Herbicide 0.75 kg/ha Antidote 1.5 kg/ha | | |
|---|---|---|---|
| Compound No. | Relative protective action in percent | Compound No. | Relative protective action in percent |
| 1 | 50 | 36 | 25 |
| 3 | 50 | 37 | 63 |
| 4 | 63 | 56 | 50 |
| 6 | 38 | 58 | 63 |
| 8 | 38 | 65 | 25 |
| 11 | 63 | 69 | 50 |
| 13 | 75 | 71 | 12.5 |
| 20 | 63 | 82 | 50 |
| 28 | 63 | 86 | 63 |
| 91 | 50 | 377 | 63 |
| 132 | 75 | 378 | 63 |
| 155 | 12.5 | 379 | 63 |
| 287 | 50 | 380 | 50 |
| 289 | 63 | 381 | 63 |
| 291 | 50 | 383 | 75 |
| 293 | 63 | 384 | 75 |
| 295 | 50 | 385 | 63 |
| 299 | 63 | 386 | 63 |
| 307 | 12.5 | 387 | 63 |
| 345 | 25 | 388 | 63 |
| 358 | 12.5 | 393 | 38 |
| 359 | 75 | 394 | 12.5 |
| 360 | 63 | 395 | 25 |
| 361 | 75 | 396 | 12.5 |
| 362 | 65 | 397 | 25 |
| 363 | 25 | 398 | 38 |
| 364 | 38 | 399 | 50 |
| 365 | 25 | 400 | 25 |
| 366 | 25 | 401 | 38 |
| 367 | 12.5 | 402 | 63 |
| 368 | 50 | 403 | 12.5 |
| 369 | 50 | 404 | 50 |
| 370 | 63 | 405 | 12.5 |
| 371 | 63 | 406 | 12.5 |
| 372 | 63 | 407 | 25 |
| 373 | 63 | 409 | 50 |
| 374 | 63 | 410 | 63 |
| 375 | 63 | 411 | 50 |
| 376 | 75 | 412 | 65 |
| 413 | 50 | 422 | 63 |
| 414 | 50 | 423 | 63 |
| 415 | 63 | 424 | 63 |
| 416 | 75 | 425 | 63 |
| 417 | 25 | 426 | 50 |
| 418 | 63 | 427 | 63 |
| 420 | 25 | 428 | 75 |
| 421 | 63 | 429 | 75 |

EXAMPLE 13

Test With Antidote and Herbicide on Barley

Barley seeds are sown in plastic pots containing 0.5 liter of garden soil in a greenhouse. After emergence of the plants to the 2- to 3-leaf stage, the substance to be tested as an antidote is applied as a tank mixture together with the herbicide 2-propinyl 2-[4-(3,5-dichloropyridyl-2-oxy)-phenyoxy]-propionate.

20 days after the application, the protective action of the antidote is rated in per cent. The plants treated with the herbicide by itself and the completely untreated controls serve as reference. The results are shown in the following tables:

TABLE 4

| Compound No. | Amounts applied:<br>Herbicide 0.25 kg/ha<br>Antidote 0.25 kg/ha<br>Relative protective action in percent |
|---|---|
| 3 | 38 |

| Compound No. | Amounts applied:<br>Herbicide 0.5 kg/ha<br>Antidote 0.5 kg/ha<br>Relative protective action in percent |
|---|---|
| 8 | 88 |

TABLE 6

Amounts applied:
Herbicide 0.5 kg/ha
Antidote 1.5 kg/ha

| Compound No. | Relative protective action in percent | Compound No. | Relative protective action in percent |
|---|---|---|---|
| 4 | 12.5 | 132 | 38 |
| 6 | 75 | 287 | 50 |
| 13 | 12.5 | 289 | 63 |
| 20 | 50 | 291 | 25 |
| 28 | 88 | 293 | 75 |
| 58 | 50 | 295 | 38 |
| 86 | 25 | 359 | 63 |
| 91 | 12.5 | 360 | 63 |
| 361 | 75 | 381 | 38 |
| 362 | 63 | 385 | 12.5 |
| 363 | 75 | 386 | 12.5 |
| 364 | 75 | 388 | 38 |
| 365 | 75 | 412 | 75 |
| 366 | 63 | 413 | 75 |
| 367 | 50 | 414 | 63 |
| 368 | 38 | 415 | 63 |
| 369 | 63 | 417 | 38 |
| 370 | 25 | 418 | 25 |
| 371 | 25 | 421 | 63 |
| 372 | 63 | 422 | 12.5 |
| 374 | 63 | 424 | 38 |
| 375 | 38 | 425 | 50 |
| 376 | 50 | 426 | 50 |
| 377 | 50 | 427 | 25 |
| 378 | 50 | 428 | 50 |
| 379 | 63 | 429 | 50 |
| 380 | 50 | | |

EXAMPLE 14

Swelling of Rice Seeds, Herbicide Applied by the Pre-Emergence Method

Rice seeds are soaked in solutions with a concentration of 100 ppm of the substance to be tested as an antidote for 48 hours. The seeds are then left to dry for about two hours, until they are not longer sticky. Plastic containers (length×width×height=25×17×12 cm) are filled with sandy loam to 2 cm below the edge. The swollen seeds are sown on the surface of the soil in the container and covered only very lightly with soil. The soil is kept in a moist (not sodden) state. The herbicide 2-chloro-2',6'-diethyl-N-[2''-(n-propoxy)-ethyl]-acetanilide is now sprayed in dilute solution onto the surface of the soil. The water level is successively increased according to the growth of the plants. 18 days after application of the herbicide, the protective action of the antidote is rated in per cent. The plants treated with the herbicide by itself and the completely untreated controls serve as a reference. The results are shown in the following table:

TABLE 7

| Antidote Compound No. | Antidote ppm | Herbicide kg of active substance/ha | Relative protective action in % |
|---|---|---|---|
| 8 | 100 | 0.25 | 50 |
| 404 | 100 | 0.25 | 38 |
| 359 | 100 | 0.25 | 25 |
| 381 | 100 | 0.25 | 63 |
| 422 | 100 | 0.25 | 63 |

EXAMPLE 15

Seed Dressing of Rice, Herbicide Applied by the Pre-emergence Method

Rice seeds are introduced into a glass container with the substance to be tested as an antidote and the components are mixed thoroughly by shaking and rotating. Containers (length×width×height=47×29×24 cm) are filled with sandy loam soil and the dressed seeds are sown in. After the seeds have been covered with soil, the herbicide 2-chloro-6'-ethyl-N-(2''-methoxy-1''-methylethyl)-acet-o-toluidide is sprayed in dilute solution onto the surface of the soil. 20 days after sowing, when the plants have reached the 3-leaf stage, the surface of the soil is covered with a layer of water 4 cm high. 30 days after application of the herbicide, the protective action of the antidote is rated in per cent. The plants treated with herbicide by itself and the completely untreated controls serve as a reference. The compounds of the formula I also show a good action in this test.

EXAMPLE 16

Seed Dressing of Rice, Herbicide Applied by the Pre-emergence Method

Rice seeds of the variety IR-36 are introduced into a glass container with the substance to be tested as an antidote and the components are mixed thoroughly by shaking and rotating. Plastic containers (length×width×height=47×29×24 cm) are filled with sandy loam soil and the dressed seeds are sown in. After the seeds have been covered with soil, the herbicide 2-chloro-6'-ethyl-N-(2''-methoxy-1''-methylethyl)-acet-o-toluidide is sprayed onto the surface of the soil. 18 days after sowing, the protective action of the antidote is rated in per cent. The plants treated with herbicide by itself and the completely untreated controls serve as references. In this test also, the compounds of the formula I have a good action.

EXAMPLE 17

Tank Mixture Applied by the Pre-emergence Method in Sorghum

Pots (upper diameter 6 cm) are filled with sandy loam soil and sorghum seeds of the 6522 variety are sown in. After the seeds have been covered with soil, the substance to be tested as an antidote is sprayed in dilute solution as a tank mixture together with the herbicide 2-chloro-6'-ethyl-N-(2''-methoxy-1''-methylethyl)-acet-o-toluidide onto the surface of the soil. 21 days after application of the herbicide, the protective action of the antidote is rated in per cent. The plants treated with herbicide by itself and the completely untreated controls serve as references. The results are shown in the following table:

TABLE 8

Amounts applied:
Herbicide 1.5 kg/ha
Antidote 1.5 kg/ha

| Compound No. | Relative protective action in percent |
|---|---|
| 402 | 50 |
| 405 | 50 |
| 409 | 38 |

EXAMPLE 18

Seed Dressing of Rice, Herbicide Applied by the Pre-emergence Method

Rice seeds are introduced into a glass container with the substance to be tested as an antidote and the components are mixed thoroughly by shaking and rotating. Containers (length × width × height = 47 × 29 × 24 cm) are filled with sandy loam soil and the dressed seeds are sown in. After the seeds have been covered with soil, the herbicide 2-propinyl 2-[4-(3,5-dichloropyridyl-2-oxy)-phenoxy]-propionate is sprayed in dilute solution onto the surface of the soil. 20 days after sowing, when the plants have reached the 3-leaf stage, the surface of the soil is covered with a layer of water 4 cm high. 30 days after application of the herbicide, the protective action of the antidote is rated in per cent. The plants treated with herbicide by itself and the completely untreated controls serve as a reference. The results are shown in the following table:

TABLE 9

| Antidote Compound No. | Antidote g of active substance/kg of seed | Herbicide kg of active substance/ha | Relative protective action in % |
|---|---|---|---|
| 3 | 0.6 | 0.25 | 50 |
|   | 0.4 | 0.25 | 63 |
|   | 0.2 | 0.25 | 63 |

EXAMPLE 19

Seed Dressing of Rice, Herbicide Applied by the Post-emergence Method

Rice seeds are introduced into a glass container with the substance to be tested as an antidote and the components are mixed thoroughly by shaking and rotating. Plastic containers (length × width × height = 25 × 17 × 12 cm) are filled with sandy loam soil and the dressed seeds are sown in. After the seeds have been covered with soil, the herbicide 2-propinyl 2-[4-(3,5-dichloropyridyl-2-oxy)-phenoxy]-propionate is applied by the post-emergence method. 21 days after the application, the protective action of the antidote is rated in per cent. The plants treated with herbicide by itself and the completely untreated controls serve as a reference. The results are shown in the following table:

TABLE 10

| Antidote Compound No. | Antidote g of active substance/kg of seed | Herbicide kg of active substance/ha | Relative protective action in % |
|---|---|---|---|
| 3 | 1 | 0.25 | 25 |
|   | 0.8 | 0.25 | 25 |
|   | 0.6 | 0.25 | 38 |

EXAMPLE 20

Seed Dressing of Rice, Herbicide applied by the Pre-emergence Method

Rice seeds of the variety IR-36 are introduced into a glass container with the substance to be tested as an antidote and the components are mixed thoroughly by shaking and rotating. Plastic containers (length × width × height = 47 × 29 × 24 cm) are filled with sandy loam soil and the dressed seeds are sown in. After the seeds have been covered with soil, the herbicide 2-propinyl 2-[4-(3,5-di-chloropyridyl-2-oxy)-phenoxy]-propionate is sprayed onto the surface of the soil. 18 days after sowing, the protective action of the antidote is rated in per cent. The plants treated with herbicide by itself and the completely untreated controls serve as references. The results are shown in the following table.

TABLE 11

| Antidote Compound No. | Antidote g of active substance/kg of seed | Herbicide kg of active substance/ha | Relative protective action in % |
|---|---|---|---|
| 3 | 0.6 | 0.25 | 50 |
|   | 0.4 | 0.25 | 63 |
|   | 0.2 | 0.25 | 63 |

EXAMPLE 21

Seed Dressing of Wheat, Herbicide Applied by the Post-emergence Method

Wheat seeds are introduced into a glass container with the substance to be tested as an antidote and the components are mixed thoroughly by shaking and rotating. Plastic containers (length × width × height = 25 × 17 × 12 cm) are filled with sandy loam soil and the dressed seeds are sown in. After the seeds have been covered with soil, the herbicide N-[(2-(2-chloroethoxy)-phenyl)-sulfonyl]-N'-(4-methoxy-6-methyl-1,3,5-triazin-2-yl)-urea is applied by the post-emergence method. 21 days after the application, the protective action of the antidote is rated in per cent. The plants treated with herbicide by itself and the completely untreated controls serve as a reference. The results are shown in the following table:

TABLE 12

| Antidote Compound No. | Antidote g of active substance/kg of seed | Herbicide kg of active substance/ha | Relative protective action in % |
|---|---|---|---|
| 8 | 0.25 | 1.0 | 25 |
|   | 0.125 | 1.0 | 25 |
|   | 0.25 | 0.5 | 12.5 |
|   | 0.125 | 0.5 | 12.5 |

EXAMPLE 22

Seed Dressing in Wheat, Herbicide Applied by the Pre-emergence Method

Wheat seeds are introduced into a glass container with the substance to be tested as an antidote and the components are mixed thoroughly by shaking and rotating. Plastic containers (length×width×height=25×17×12 cm) are filled with sandy loam soil and the dressed seeds are sown in. After the seeds have been covered with soil, the herbicide N-[(2-(2-chloroethoxy)-phenyl)-sulfonyl]-N'-(4-methoxy-6-methyl-1,3,5-triazin-2-yl)-urea is sprayed onto the surface of the soil. 21 days after application of the herbicide, the protective action of the antidote is rated in per cent. The plants treated with herbicide by itself and the completely untreated controls serve as a reference. The results are shown in the following table:

TABLE 13

| Antidote Compound No. | Antidote g of active substance/kg of seed | Herbicide kg of active substance/ha | Relative protective action in % |
| --- | --- | --- | --- |
| 8 | 0.25 | 1.0 | 25 |
|   | 0.125 | 1.0 | 25 |
| 8 | 0.25 | 0.5 | 25 |
|   | 0.125 | 0.5 | 25 |
| 8 | 0.25 | 0.25 | 12.5 |
|   | 0.125 | 0.25 | 12.5 |

EXAMPLE 23

Increase in Yield by Grown Regulation in Soybean

Soybeans of the "Hark" variety are sown in plastic containers containing a soil/peat/sand mixture in the ratio 6:3:1 and are kept in a climatically controlled chamber under optimum conditions in respect of temperature, illumination, fertilisation and watering. The plants develop thus to the 5- to 6-trifoliate leaf stage in about 5 weeks. In this stage of development, the plants are sprayed with the aqueous liquor of an active substance of the formula I until they are thoroughly wet. The active substance concentration is 500 ppm. Evaluation is carried out 5 weeks after application of the active substance. In comparison with untreated control plants, the plants treated with active substances of the formula I according to the invention display a noticeable increase in the number and weight of silicules harvested. Compounds No. 58, 295 and 378 prove to be particularly effective.

EXAMPLE 24

Promotion of Root Growth in Wheat and Soybean

Compound of the formula I are used as an aqueous dispersion obtained from a 25% wettable powder. The test is carried out on seeds which have been sown in plastic cylinders 5×30 cm filled with soil (10 seeds per cylinder), a) the seeds being treated in application amounts of 4—1340 mg per kg of seed before being sown, or b) untreated seed being sown and the soil being sprayed with the active substance dispersion in application amounts of 0.3 to 3 kg per hectare. The cylinders are kept in a climatically controlled chamber, under controlled conditions. After 10 days, the seedlings are free from the soil by careful washing with water and the length and dry weight of the roots are measured. Of the compounds of the formula I, compounds No. 364 and 369 in particular have a good action in this test.

What is claimed is:

1. A method of protecting a cultivated plant from the harmful effects of a herbicide, comprising the step of treating said plant, part thereof or locus thereof with said herbicide, which is selected form the group consisting of triazines, triazinones, ureas, phenylureas, sulfonylureas, carbamates, thiocarbamates, halogenoacetanilides, chloroacetamides, halogenophenoxyacetic acid esters, diphenyl ethers, pyridyloxyphenoxyacetic acid esters, pyridyloxyphenoxyacetic acid amides, pyridyloxyphenoxypropionic acid esters, pyridyloxyphenoxypropionic acid amides, benzoic acid derivatives, nitroanilines, oxadiazolones, phosphates and pyrazolones, and an antagonistically effective amount of a compound of the formula

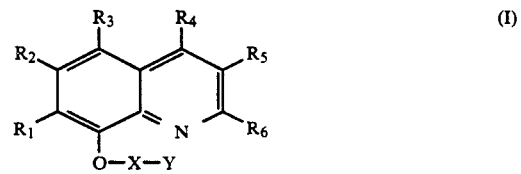

in which $R_1$, $R_2$, $R_4$, $R_5$ and $R_6$ are hydrogen, $R_3$ is hydrogen or chlorine, X is —$CH_2$— or —$CH(CH_3)$— and Y is —$COOR_7$, —$COSR_8$ or —$CONR_9R_{10}$, wherein $R_7$ is hydrogen; an alkali metal cation or a quaternary ammonium cation; $C_1$–$C_{18}$-alkyl; $C_1$–$C_{10}$-alkyl which is substituted by halogen, nitro, cyano, hydroxyl, $C_1$–$C_8$-alkoxy, $C_1$–$C_4$-alkoxyethoxy, $C_2$–$C_6$-hydroxyalkoxy, $C_2$–$C_6$-hydroxyalkylthio, $C_1$–$C_4$-alkoxycarbonyl, $C_2$–$C_{12}$-dialkylamino or phenoxy; $C_1$–$C_6$-alkyl, which is substituted by phenyl, tetrahydrofuranyl, tetrahydropyranyl, furanyl, morpholinyl, piperidinyl, pyridinyl or phenyl which is substituted by $C_1$–$C_3$-alkoxy; $C_3$–$C_{10}$-alkenyl; $C_3$–$C_6$-alkynyl, which is unsubstituted or substituted by halogen or hydroxyl; $C_3$–$C_8$-cycloalkyl, which is unsubstituted or substituted by $C_1$–$C_3$-alkyl; phenyl, which is unsubstituted or substituted by one or two halogen, nitro, $C_1$–$C_4$-alkyl or $C_1$–$C_4$-alkoxy or naphthyl; $R_8$ is hydrogen; $C_1$–$C_{18}$-alkyl; $C_1$–$C_{10}$-alkyl which is substituted by $C_1$–$C_4$alkoxycarbonyl; or phenyl, which is unsubstituted or substituted by halogen; $R_9$ is hydrogen; $C_1$–$C_{18}$-alkyl; $C_2$–$C_6$-alkyl which is substituted by halogen, hydroxy, $C_1$–$C_6$-alkyl-amino, $C_2$–$C_8$-dialkylamino, $C_2$–$C_6$-hydroxyalkylamino, $C_2$–$C_6$-di-(hydroxyalkyl)-amino, $C_2$–$C_6$-aminoalkylamino or $C_1$–$C_4$-alkoxycarbonyl; $C_1$–$C_4$-alkyl, which is substituted by cyano, $C_1$–$C_4$-alkoxy, tetrahydrofuranyl, morpholinyl, pyridyl, thizaolyl, piperidinyl or phenyl which is unsubstituted or substituted by halogen; $C_1$–$C_3$-alkoxy; $C_3$–$C_6$-alkenyl; $C_3$–$C_8$-cycloalkyl, phenyl, which is unsubstituted or substituted by halogen, nitro, cyano, $C_1$–$C_4$-alkyl, $C_1$–$C_4$-alkoxy or $C_1$–$C_2$-halogenoalkyl; and $R_{10}$ is hydrogen; $C_1$–$C_6$-alkyl; $C_1$–$C_6$-alkoxyalkyl; $C_3$–$C_6$-alkenyl; $C_3$–$C_6$-cycloalkyl; or phenyl; or in which $R_9$ and $R_{10}$, together with the nitrogen atom to which they are bonded, are an imidazolyl, oxazolinyl, pyrimidinyl, morpholinyl or piperidinyl ring, including herbicidally acceptable acid addition salts and metal complexes thereof.

2. The method of claim 1 wherein Y is —$COOR_7$.

3. The method of claim 1 wherein the compound of the formula is 2-(5-chloroquinolin-8-yloxy)-acetic acid-(1-methylhexyl) ester.

4. The method of claim 1 wherein the herbicide is a diphenyl ether.

5. The method of claim 1 wherein the herbicide is a substituted pyridyloxyphenoxypropionic acid ester.

6. The method of claim 5 wherein the substituted pyridyloxyphenoxypropionic acid ester is 2-propynyl 2-[4-(3,5-dichloropyridyl-2-oxy)-phenoxy]-propionate.

7. The method of claim 1 wherein the cultivated plant is a cereal.

8. The method of claim 1 wherein the herbicide is selected from the group consisting of sulfonylureas, pyridyloxyphenoxypropionic acid esters, pyridyloxyphenoxypropionic acid amides, benzoic acid derivatives, nitroanilines, oxadiazolones, phosphates and pyrazolones.

* * * * *